United States Patent [19]

Ishikawa et al.

[11] Patent Number: 4,484,993

[45] Date of Patent: Nov. 27, 1984

[54] PROCESS FOR PRODUCING FLUORINE-CONTAINING ORGANIC COMPOUND

[75] Inventors: Nobuo Ishikawa, Yokohama; Tomoya Kitazume, Tokyo, both of Japan

[73] Assignee: Daikin Kogyo Co., Ltd., Osaka, Japan

[21] Appl. No.: 416,493

[22] Filed: Sep. 10, 1982

[30] Foreign Application Priority Data

| Sep. 10, 1981 [JP] | Japan | 56-143109 |
| Nov. 26, 1981 [JP] | Japan | 56-189458 |
| Nov. 26, 1981 [JP] | Japan | 56-189459 |
| Mar. 8, 1982 [JP] | Japan | 57-36129 |

[51] Int. Cl.³ ............................................. B01J 19/10
[52] U.S. Cl. ............................................. 204/158 HA
[58] Field of Search ......... 204/158 HA, 158 S, 163 R

[56] References Cited

U.S. PATENT DOCUMENTS 3,184,400  5/1965  Magnus ............................ 204/158 S
3,630,866  12/1971 Pelofsky ........................... 204/158 S

OTHER PUBLICATIONS

Keller et al., Journal of Fluorine Chemistry, 6, (1975), pp. 297–310.
Chambers et al., Journal of the Chemical Society, (1962), pp. 1993–1999.

Primary Examiner—Howard S. Williams
Attorney, Agent, or Firm—Armstrong, Nikaido, Marmelstein & Kubovcik

[57] ABSTRACT

A process for producing fluorine-containing organic compounds characterized in that fluorine-containing aliphatic iodides which comprise at least one selected from the group of $R_fI$, $R_fZnI$ and $R_fSnX_2I$ (where $R_f$ indicates a fluorine-containing aliphatic group; and X indicates halogen), or which comprise $R_fCOOR'$ (where $R_f$ indicates a fluorine-containing aliphatic group; and R' indicates an aliphatic hydrocarbon group or aromatic hydrocarbon group) are reacted with organic compounds under ultrasonic wave action, whereby the $R_f$ group or the $R_fCO$ group is introduced into the said organic compounds.

29 Claims, No Drawings

PROCESS FOR PRODUCING FLUORINE-CONTAINING ORGANIC COMPOUND

BACKGROUND OF THE INVENTION

1. Field of the Invention

This invention relates to a process for producing fluorine-containing organic compounds.

2. Description of the Prior Art

Compounds containing fluorine have versatile useful applications by virtue of their superior stability, chemical resistance, weather resistance, water and oil repellent properties, physiological activity and so on. A variety of studies have been made on the compounds containing the fluorine-containing alkyl group within their molecules, and several new synthesizing methods have been hitherto developed.

There are reported of the synthesizing methods; for the compounds containing trifluoromethyl group, the followings may be mentioned, (1) a method to directly fluorinate the methyl group with metallic fluorides, (2) an halogen exchange reaction on $CCl_3$ group with $HF$-$SbCl_5$, (3) a method to fluorinate $COOH$ group with $SF_4$, (4) radical reaction to introduce a $CF_3$ group into heterocyclic compounds, (5) a method to substitute iodine which is introduced into aromatic compounds for Rf by means of RfCuI (Ullmann-type reaction) (Rf indicates fluorine-containing aliphatic group: hereinafter it is so represented).

Further, it is known that the trifluoromethyl magnesium iodide ($CF_3MgI$) can not be used for trifluoromethylation reaction in that the compound is very unstable due to its property to eliminate $MgF_2$ by readily extracting F because its constituent Mg is highly bondable with F.

Among above-described synthesizing methods for trifluoromethyl-containing compounds, the methods other than the Ullmann-type reaction, the reagent for fluorination is highly hazardous, and that its handling is difficult, and that it is hard to optionally introduce the trifluoromethyl group into a desired position in a molecule.

Conversely, there is reported that β-keto carboxylic acid ester can be synthesized by applying the Reformatsky reaction on ester compounds.

However, the reaction is difficult and less successful instances are known up to the present. The details are explained as follows:

Firstly, α-carboxylic acid ester (1) is caused to react with zinc in accordance with the following reaction, then a Reformatsky-type reagent (2) is obtained.

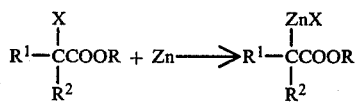

1 ($R^1$, $R^2$: alkyl group,   2 (R: alkyl group)
X: Br)

In this case, it is undesirable when the raw material, ester (1) and the product, ester (2), are condensated, and

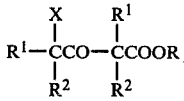

is produced. Thus, it was a prerequisite to handle them without generating the above result (or preventing the reaction of both esters).

Accordingly, in obtaining an end product β-ketocarboxylic acid ester (4) by subjecting the above-described reagent (2) to reaction with a ester compound (3) with the following formula, due to the above prerequisite, it becomes difficult to cause the reaction itself of the ester (2) with the ester (3).

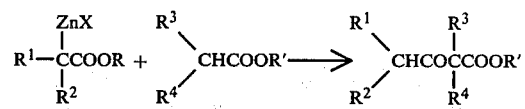

2   3 ($R^3$, $R^4$, R': alkyl group)

Thus, it is necessary to select an ester that may easily react with the reagent (2) without self-condensation between the ester (1) and (2).

This is a reason why there have been almost no successful experimental results in the synthesizing of the compound as intended.

In consequence, even when the fluorine-containing ester which is represented by $R_fCOOR'$ ($R_f$: fluorine-containing alkyl group is employed as the above-described ester compound (3) so as to introduce fluorine into the object compound, it is not easy to obtain a fluorine-containing alkyl keto carboxylic acid ester by means of the said Reformatsky reaction.

OBJECTS AND SUMMARY OF THE INVENTION

Accordingly, the primary object of this invention is to present a method in which the reaction for introducing the fluorine-containing group into the organic compound can proceed in an easy and safety under the normal conditions.

The secondary object of the invention is to present a method for synthesizing organic compounds containing a fluorine-containing aliphatic group, such as trifluoromethyl group in particular, with good yield and in a stabilized fashion.

Further, the third object of the invention is to present a method for introducing various RfCO groups into the intended compounds at the specified position preferentially and a high yield rate under mild conditions by applying the Reformatsky reaction.

The process of the present invention to produce fluorine-containing organic compounds is characterized in the introduction of Rf group into the above-said organic compounds by subjecting the fluorine-containing aliphatic iodides which are represented by $R_fI$, $R_fZnI$, or $R_fSnX_2I$ (where $R_f$ indicates the fluorine-containing aliphatic group; X indicates halogen), and organic compounds to reaction under the action of ultrasonic waves.

The present invention is related to the process for producing fluorine-containing diketones, and characterized, as an application of the Reformatsky reaction, to have (1) a process to generate a metallic halogenated ketone which is represented by the formula:

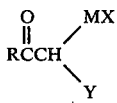

(where R: aliphatic hydrocarbon-oxy group, or aliphatic hydrocarbon group, or fluoro aliphatic hydrocarbon group which may form a ring with the carbon atoms being bonded with X; X: halogen; Y: hydrogen atom or fluorine atom; and M: zinc or magnesium) by causing the halogenated ketone represented by the Formula:

(where R,X and Y are same as the above definition)to reaction with the metal consisting of zinc or magnesium, and to have (2) a process to generate the fluorine-containing diketones which represented by the Formula:

(where R and Y are as described before, and $R_f$ is fluoroaliphatic hydrocarbon group and includes those containing ether bonds within the chain), by causing the metallic halogenated ketone to react with the fluoroester which is represented by the Formula:

(where $R_f$ is as described above, and R' is aliphatic hydrocarbon group or aromatic hydrocarbon group), under the action of ultrasonic waves.

DESCRIPTION OF THE PREFERRED EMBODIMENT

The method of the present invention is exemplified as follows.

The fluorine-containing aliphatic iodide which is represented by the Formula:

(where $R_f$ indicates the fluorine-containing aliphatic group), and the carbonylic compound which is represented by the Formula:

(where R and R': similar or dissimilar atom or group selected from the group comprising the hydrogen atom, aliphatic group and aromatic group, and can form a ring jointly where both of them are of aliphatic groups), are caused to react in the presence of zinc powder and halogenated tin powder which is represented by the Formula:

(where X indicates the halogen like chlorine, bromine and iodine, etc.) by being subjected to ultrasonic waves. (where the halogenated tin powder is employed, it is effective in the presence of the tertiary amine, in place of the environment of the action of ultrasonic waves). Following the above reaction, the fluorine-containing carbinol which is represented by the Formula:

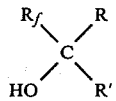

(where $R_f$, R and R' are the same as above), is formed by subjecting the reaction product to hydrolysis.

Namely, the reaction in accordance with the present invention is capable to synthesize the fluorine-containing carbinol with a high yield and in a stabilized fashion, when the raw material $R_fI$ and RCOR' undergo reaction, preferably in the presence of the zinc powder and/or the halogenated tin powder, within a reactor, in the presence of the action of ultrasonic waves, by causing the interaction between molecules, and thereby cross-coupling RCOR' with $R_fI$, and thereafter causing hydrolysis. This reaction is conjectured that, for instance, where the zinc powder is employed (it is similar with the halogenated tin powder), the reaction may proceed as follows:

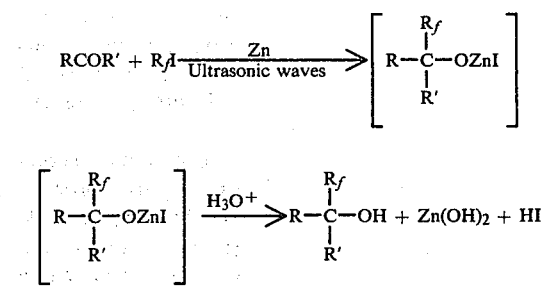

In this case, it is thought that the above-said intermediate product may be produced, in that the Zn powder (and/or halogenated tin powder) produces a stabilized $R_fZnI$ (and/or $R_fSnX_2I$) by first reacting with the reaction substance, particularly $R_fI$, and then the product is caused to have a full interaction with RCOR'.

Namely, with the method of this invention, although the mechanism is not fully clarified at present, it is thought that the interaction between the reaction molecules is made closer with the action of ultrasonic waves as given above, and thereby accelerates the generation of the above-mentioned intermediate product.

Where the halogenated tin is employed, it is also effective to cause the reaction under the addition of the tertiary amine (i.e., pyridine, triethylamine, N, N-dimethylaniline) instead in the presence of ultrasonic waves. It is thought that the tertiary amine is coordinated at Sn position of $R_fSnIX_2$ and activates the $R_f$-Sn bonding.

Where the ultrasonic wave or the tertiary amine is not present, it is experimentally confirmed that the reaction does not proceed entirely.

What is important with the method of this invention is represented by the employment of Zn and/or $SnX_2$ (where X: halogens such as chlorine, bromine and iodine, etc.) for the above-said cross coupling. This reaction appears to be similar to the publicly known Grignard reaction. However, where Mg or Li is employed, $R_fMgI$ (or $R_fLi$) itself is extremely unstable to produce the above-said intermediate product, thus it precludes its use for the synthesizing reagent. In other words, Mg or Li has a strong affinity toward F. Where Mg (or Li) is caused to react with $R_fI$, $MgF_2$ or $LiF$ is eliminated from $R_fMgI$ or $R_fLi$, resulting in the production of fluoroalkene. Thus the Grignard reagent (or $R_fLi$) such as $R_fMgI$ can not be used for the present invention.

This fact indicates the characteristics or speciality of the present invention which introduces a fluorine-containing aliphatic group. Furthermore, with the method of this invention, the raw materials are stabilized respectively, and also the reaction can be implemented within a single reaction vessel under the normal conditions subject to the ambient temperature and atmospheric pressure. Thus, handling is easier handling and most practicable.

For the method of this invention, as the usable $R_fI$, the fluorine-containing aliphatic iodides which are represented by the Formula, $CF_3(CF_2)_nI$ or $(CF_3)_2CF(CF_2)_nI$ can be noted. These include: $CF_3I$, $CF_3CF_2I$, $CF_3(CF_2)_2I$, $CF_3(CF_2)_3I$, $CF_3(CF_2)_4I$, $CF_3(CF_2)_5I$, $(CF_3)_2CFI$, $(CF_3)_2CFCF_2I$, $(CF_3)_2CF(CF_2)_2I$ and $(CF_3)_2CF(CF_2)_3I$. Other than these alkyl groups, the method can use the unsaturated group, especially the iodides consisting of the alkenyl group, such as $CF_2=CF-CF_2I$ and $CF_3-CF=CFI$. However, it is advisable that the number of carbon atoms in the fluorine-containing aliphatic iodides to be used should be at 10 or less, taking into account the solubility against solvents. For the above-mentioned fluorine-containing aliphatic iodides which can be used, $CF_3(CF_2)_2CH_2CF_2I$ that is bonded with hydrogen atoms in the molecular chain, is usable in addition to the above-enumerated perfluoroalkyl group or alkenyl group. In this case, it is necessary that F should be present adjacent to I. Also diiodides, i.e., $I(CF_2CF_2)_nI$ can be used. Further, other than the above $R_fI$, aromatic group substituted iodides, i.e. $C_6H_5-CF_2I$, $C_6H_5-(CF_2)_2I$, may be used.

As RCOR' to be employed for the method of the present invention, the following compounds may be used:

(1) aliphatic aldehydes including: HCHO, $CH_3CHO$, $C_2H_5CHO$, $C_3H_7CHO$, $C_4H_9CHO$, $C_5H_{11}CHO$, $CH_2=CHCHO$, $CH_3CH=CHCHO$, $(CH_3)_2C=CHCHO$, etc.;

(2) aromatic aldehyde including: $C_6H_5CHO$, $C_6H_5CH=CHCHO$, $CH_3OC_6H_5CHO$;

(3) aliphatic ketones including: $CH_3COCH_3$, $CH_3COC_2H_5$, $(C_4H_9)_2CO$, $CH_2=CHCOCH_2CH_3$, $(CH_3)_2C=CHCOCH_3$;

(4) aromatic ketones including:

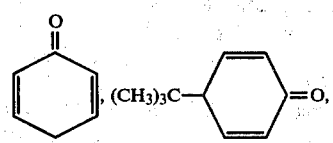, $(CH_3)_3C-$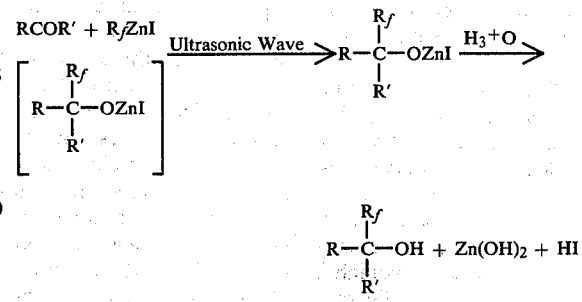

$C_6H_5COCH_3$, $C_6H_5COCH=CH_2$ R and R' in RCOR' are a similar or dissimilar atom or group, and it is permitted to use the above-stated saturated or unsaturated compounds, in addition to those introduced with a substitute group into their parts. When R and R' are of aliphatic groups, it is advisable to limit the number of carbon atoms to 15 or less, taking into considerations the solubility into solvents, and also to be capable to form rings jointly, especially cyclohexylic rings.

For the method of the present invention, it is preferable to add the above-mentioned zinc powder or $SnX_2$ powder within a range of one to three times the number of moles against $R_fI$, so as to make the reaction proceed fully and appropriately. These metallic reagents may be used independently or jointly. Where the reagents are used jointly, it is preferable to add the total amount of zinc powder and $SnX_2$ powder within a range of one to three times the number of moles against $R_fI$.

It will serve the purpose of the present invention of the reaction may continue, to the full extent, even if ambient temperature and atmospheric pressure are used; and if a range of ultrasonic waves, which is obtained with a commercially available ultrasonic cleaner, is employed. The tertiary amine, which is added under when halogenated tin is employed, may be of one fifths (percentage by volume) of an amount of the solvent to be used. For solvents to be used in the reaction system, it is recommended to employ aprotic solvents, such as dimethylformaldehyde, tetrahydrofuran, dimethylsulfoxide, dimethylacetamide, N-methyl-pyrrolidone, hexamethylphosphoamide, and acetonitrile.

These polar solvents have a strong dissolving action in that they have a high solvation energy against cations, and act to increase a reaction rate of anionic reagents.

For the method of the present invention, where the initiating substance itself is a liquid, it is not always necessary to use the above-mentioned solvents. And for the hydrolysis to obtain carbinol, ordinary mineral acids such as HCl and $H_2SO_4$ may be used.

The inventors have also found out that the following reaction is able to synthesize a fluorine-containing carbinol in a stabilized fashion and with a good yield, in addition to the above-described synthetic reaction.

That is, the method uses $R_fZnI$ or $R_fSnX_2I$ ($R_f$ and X are similar to those described before) (or jointly uses $R_fZnI$ and $R_fSnX_2I$) instead of the above-given $R_fI$. The substance is subjected to reaction with RCOR' (R and R' are similar to those described before) particularly in the presence of the action of ultrasonic waves (where $R_fSnX_2I$ is employed, or it may be subjected to a reaction under the conditions where the above-given tertiaryamine is added).

Thence, where the product is subjected to hydrolysis, carbinol can be obtained as in the above-described case. This reaction can be represented as follows for a case where $R_fZnI$ is used.

$$RCOR' + R_fZnI \xrightarrow{\text{Ultrasonic Wave}} \left[ \begin{array}{c} R_f \\ | \\ R-C-OZnI \\ | \\ R' \end{array} \right] \rightarrow R-\underset{\underset{R'}{|}}{\overset{\overset{R_f}{|}}{C}}-OZnI \xrightarrow{H_3^+O}$$

$$R-\underset{\underset{R'}{|}}{\overset{\overset{R_f}{|}}{C}}-OH + Zn(OH)_2 + HI$$

According to this reaction, it is characteristic to cause $R_fZnI$ and/or $R_fSnX_2I$ which was previously synthesized to react with carbonyl compounds. Also in this case, it is considered that, similar to the above description, the action of the ultrasonic waves or the tertiary amine may cause the closer interaction between reacting molecules, and accelerate the generation of the intermediate product as mentioned before. Namely, due to the coordinate action of the ultrasonic-wave energy or the tertiary amine, it is considered that the bonding of $R_f$-Zn or $R_f$-Sn of $R_f$ZnI or $R_f$SnX$_2$I in particular may be made weaker, and the interaction with RCOR' may be strengthened, thereby the interaction may proceed to the full extent.

$R_f$ZnI or $R_f$SnX$_2$I, itself, which is used, easily dissolves into the given solvents, and causes the reaction to proceed in an easier manner. And this $R_f$ZnI or $R_f$SnX$_2$I can be synthesized within an autoclave at a temperature at 120° to 150° C. by causing the reaction of the above-stated $R_f$I with Zn or SnX$_2$ powder (X: halogen).

In this case, it is desirable to use an amount of Zn or SnX$_2$ at one to three times the number of moles against $R_f$I. Zn and SnX$_2$ may be used simultaneously, but it is preferable that their total amount is set at one to three times the number of moles against $R_f$I.

The solvent to be used for the reaction and the conditions for reaction with carbonyl compounds are similar to that of the description previously given.

The fluorine-containing carbinol which is synthesized according to the method of the present invention, is most useful and can be used for the applications as follows:

(1) the substance itself can be used as a solvent,
(2) the substance can be used as a synthetic intermediate for water or oil repellent agents, medicines, agricultural chemicals, dyes, surface active substance, etc.,
(3) the substance can be used as a monomer to produce fluorine-containing polymers. For instance, it forms an unsaturated bonding of a monomer by removing OH group and adjacent hydrogen atoms by means of dehydration reaction.

The method of the present invention may be based on the following reaction. That is, a fluorine-containing aliphatic iodide which is represented by the Formula, $R_f$I (where $R_f$: fluorine-containing aliphatic group), and a halogen-substituted aliphatic unsaturated compound or a halogen-substituted aromatic compound is subjected to a reaction in the presence of ultrasonic wave action and in the presence of zinc powder and a palladium catalyst. This introduces the above-said $R_f$ into the above multiple bond or the benzene nucleus of the unsaturated aliphatic compound or an aromatic compound, from which above-said halogen eliminated.

According to this method, where the initiating substance, $R_f$I, and a halogen-substituted unsaturated aliphatic compound or a halogen-substituted aromatic compound are caused to react with each other; namely, when these substances are subjected to the action of ultrasonic waves by bringing them into contact with the palladium catalyst in the presence of the zinc powder, the interaction between the reacting molecules is made closer by the ultrasonic-wave energy, whereby $R_f$I is efficently cross-coupled with the above-stated multiple bonding position or carbon atoms of the benzene nucleus, and finally it is possible to obtain with a good yield, a product which is introduced with the fluorine-containing aliphatic group ($R_f$) under the condition of dehalogenation. In this case, the Zn powder firstly reacts with $R_f$I, resulting with the stabilized $R_f$ZnI, and also, reacts by maintaining the full interaction with the halogen-substituted unsaturated aliphatic compound or aromatic compound which is activated under the action of the palladium-type catalyst.

Conversely, where the palladium-type catalyst is is not used and the ultrasonic wave is not put into action, it is ascertained that no reaction does proceed.

It is considered that the above-described reaction may proceed as below, where the halogenated allyl is employed instead of the above-stated halogenated aliphatic unsaturated compound.

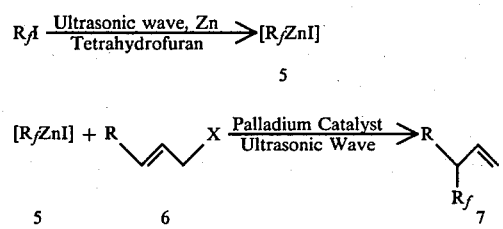

That is, with the reaction of $R_f$I with Zn, the intermediate product (5) (i.e. perfluoroalkyl zinc iodide) is generated, and the perfluoroalkylated substance (7) of a halogenated allyl is produced through smooth reaction of the halogenated allyl (6) (where R: alkyl group; X: halogen) with the intermediate product (5) within the said solvent (in situ) in the presence of the palladium-type catalyst. This perfluoroalkyl group is introduced into the γ-position of the halogenated allyl (6) under the dehalogenation (X) condition at a probability of 95% or greater in a position-selective fashion, and thereby the desired product (7) bonded selectively at the γ-position with $R_f$ can be obtained with a good yield.

As the palladium-type catalysts to be used for this reaction, various types of them were tried. Namely, various palladium-type catalysts were applied at the reaction, for instance, of trifluoromethyl zinc iodide (corresponding to the above 5) and cinnamyl bromide (corresponding to the above 6). It was found out that the palladium acetate (Pd(OA$_c$)$_2$) was particularly best suited to the aspect of yield of the product as indicated on the following Table 1.

TABLE 1

| Catalyst | Yield (%)*[1] |
|---|---|
| Pd(OA$_c$)$_2$ | 63 |
| PdCl$_2$ | 34 |
| PdCl$_2$(PPh$_3$)$_2$*[2] | 51 |
| PdCl$_2$(PhCN)$_2$*[3] | 23 |

*[1]The measurement value by means of 19$_F$NMR adopting PhCF$_3$ as a comparative substance.
*[2]Bis (triphenylphosphine)palladium dichloride.
*[3]Bis (benzonitrile)palladium dichloride.

For this method, as a usable $R_f$I, it can include the fluorine-containing aliphatic iodides which are represented by the Formula, CF$_3$(CF$_2$)nI or (CF$_3$)$_2$(F$_2$)nI. Included are: CF$_3$I, CF$_3$CF$_2$I, CF$_3$(CF$_2$)$_2$I, CF$_3$(CF$_2$)$_3$I, CF$_3$(CF$_2$)$_4$I, CF$_3$(CF$_2$)$_5$I, (CF$_3$)$_2$CFI, (CF$_3$)$_2$CFCF$_2$I, (CF$_3$)$_2$CF(CF$_2$)$_2$I, and (CF$_3$)$_2$CF(CF$_2$)$_3$I, etc. In addition to these alkyl groups, unsaturated groups, particularly, the iodides consisting of alkenyl groups, for instance, CF$_2$=CF-CF$_2$I and CF$_3$-CF=CFI, may be used, provided that the number of carbon atoms of the fluorine-containing aliphatic iodides to be used is preferably at 10 or less in consideration of the solubility against solvents. Further, as the said fluorine-containing aliphatic iodides, in addition to the above-enumerated perfluoroalkyl group or alkenyl group, CF$_3$(CF$_2$)$_2$CH$_2$CF$_2$I which is bonded with the hydrogen atoms at a part of the molecular chain may be used. In this case, it is necessary that F is present adjacent to I. Also, diiodides such as I(CF$_2$CF$_2$)$_n$I may be used.

Further, in addition to the above-said R$_f$I, aromatic group-substituted iodides such as C$_6$H$_5$-CF$_2$I and C$_6$H$_5$-(CF$_2$)$_2$I may be used.

And as the usable halogenated aliphatic unsaturated compounds, including the above-mentioned allyl bromides, halogenated allyl compounds or their derivatives which are represented by the following Fomula may be included.

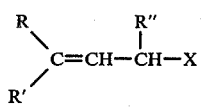

(where R, R' and R" indicate an hydrogen atom, alkyl group or alkenyl group, having carbon atom numbers of 10 or less than 10, aromatic group or aromatic group substituted with substituents, X: halogens such as Br, I and Cl.)

Here, as R, R' and R", the alkyl groups such as methyl group, ethyl group, propyl group, isopropyl group, butyl group; and alkenyl groups which have unsaturated bond partially may be applied. But, it is preferable that the number of carbon atoms be at 10 or less. Also, as the substituent to be introduced into the above-stated substituted aromatic group, it is necessary to employ the substituents which will not substantially affect the development in the dehalogenating reaction. As such substituent, alkyl group or alkenyl group may be adopted. In this case, the number of carbon atoms therein is preferred to be limited to 5 or less. And, other types of substituents to be introduced into these aromatic groups may be of aryl group, halogens such as Cl, nitro group, cyano group, and alkoxy group.

Also, it is possible to use the halogenated vinyl compounds or their derivatives which are represented by the following Formula, instead of the above given halogenated allyl compounds or their derivatives.

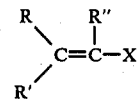

(where R, R' and R" are similar to those described before. X indicates the halogens such as Br, I, Cl and etc.)

In this case, against the α-position (vinylic position) of the halogenated vinyl compounds or their derivatives, R$_f$ will be introduced selectively as follows under the conditions of dehalogenation (X). Tetrakis (triphenylphosphine) palladium may be used as the palladium-type catalyst.

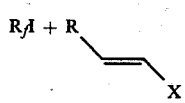

Ultrasonic wave, Zn/Tetrahydrofuran (solvent) / Pd(PPh$_3$)$_4$ →

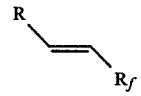

Thus, by using various R$_f$I and derivatives of halogenated allyl or vinyl compounds, their perfluoroalkylation was made according to the method of the present invention, the results indicated on the following Table-2 were obtained.

TABLE 2

| R$_f$ | Substrate | Product*[1] | Catalyst | Reaction Time (hr) | Yield (%) | Boiling Point (°C./mmHg) |
|---|---|---|---|---|---|---|
| CF$_3$ | PhCH=CHCH$_2$Br | Ph(CF$_3$)CHCH=CH$_2$*[2] | Pd(OAc)$_2$ | 1 | 63 | 81~83/25 |
| CF$_3$ | PhCH=CHBr | PhCH=CHCF$_3$ | Pd(PPh$_3$)$_4$ | 1 | 65 | 70~72/25 |
| CF$_3$ | 4-CH$_3$C$_6$H$_4$CH=CHBr | 4-CH$_3$C$_6$H$_4$CH=CHCF$_3$ | Pd(PPh$_3$)$_4$ | 1 | 67 | 59~60*[3] |
| CF$_3$ | 4-CH$_3$C$_6$H$_4$CH=CHCH$_2$Br | 4-CH$_3$C$_6$H$_4$(CF$_3$)CHCH=CH$_2$ | Pd(OAc)$_2$ | 1 | 67 | 90~92/26 |
| n-C$_3$F$_7$ | PhCH=CHCH$_2$Br | Ph(C$_3$F$_7$$^n$)CHCH=CH$_2$*[2] | PD(OAc)$_2$ | 0.5 | 71 | 81~83/21 |
| n-C$_3$F$_7$ | PhCH=CHBr | PhCH=CHC$_3$F$_7$*[2] | Pd(PPh$_3$)$_4$ | 1 | 66 | 78~80/24 |
| i-C$_3$F$_7$ | PhCH=CHCH$_2$Br | Ph(C$_3$F$_7$$^i$)CHCH=CH$_2$*[2] | Pd(OAc)$_2$ | 0.5 | 78 | 80~82/21 |
| i-C$_3$F$_7$ | PhCH=CHBr | PhCH=CHC$_3$F$_7$$^{i*[2]}$ | Pd(PPh$_3$)$_4$ | 1 | 72 | 75~77/24 |
| n-C$_4$F$_9$ | CH$_3$CHCHCH$_2$Br | CH$_3$(C$_4$F$_9$$^n$)CHCH=CH$_2$*[2] | Pd(OAc)$_2$ | 0.5 | 68 | 81~84*[3] |
| n-C$_4$F$_9$ | PhCH | PhCH=CHC$_4$F$_9$$^{n*[2]}$ | Pd(PPh$_3$)$_4$ | 1 | 62 | 76~78/23 |

TABLE 2-continued

| $R_f$ | Substrate | Product*[1] | Catalyst | Reaction Time (hr) | Yield (%) | Boiling Point (°C./mmHg) |
|---|---|---|---|---|---|---|
| | =CHB$_r$ | | | | | |

*[1]: The structure of products was identified with IR, NMR and mass spectrometry.
*[2]: This is a new compound, and its elementary analysis result has fully coincided with the calculated value. (C, H, N: ± 0.4).
*[3]: Indicates the melting point (°C.).

Among the above-given new compounds (*2), the identified data (NMR) of the allyl compound are specifically given below.

Ph(CF$_3$)CHCH=CH$_2$:
$^1$H NMR: τ 5.2, 5.0, 5.9 (CH=CH$_2$) 4.7 (CH(CF$_3$)) 7.5 (AR—H)
$^{19}$F NMR: −22 (CF$_3$COOH is determined to be the external standard)
Ph(C$_3$F$_7{}^n$)CHCH=CH$_2$:
$^1$H NMR: τ 5.8, 5.2, 5.1 (CH=CH$_2$) 4.6 (CH—) 7.4 (AR—H)
$^{19}$F NMR: −9.0 (CF$_2$) 1.5 (CF$_3$) 41.0 (CF$_2$)
Ph(C$_3$F$_7{}^i$)CHCH=CH$_2$:
$^1$H NMR: τ 6.1, 5.4, 5.2 (CH=CH$_2$) 4.8 (CH—) 7.5 AR—H)
$^{19}$F NMR: −7.0 (CF$_3$) 102 (CF)
CH$_3$(C$_4$F$_9{}^n$)CHCH=CH$_2$:
$^1$H NMR: τ 6.5, 6.2, 5.0 (CH=CH$_2$) 1.6 (CH$_3$) 4.7 (CH—)
$^{19}$F NMR: −4.0, 36.0, 40.0 (CH$_2$) 3.1 (CF$_3$)

Further, instead of the above-described halogenated aliphatic unsaturated compounds, the halogenated aryl compounds or their derivatives as the halogen-substituted aromatic compounds which are represented by the following Formula may be used.

In this case, with the carbon atoms which are bonded with the halogen, the cross coupling is generated.

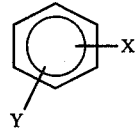

(where X indicates halogens such as Br, I and Cl; Y indicates at least one type of the substituent or hydrogen atom, which is selected from the groups consisting of alkyl group or alkenyl group having carbon atom numbers of 5 or less, or cyano group, nitro group, ester group and aryl group.)

Here, as Y, the alkyl group or alkenyl group such as methyl group and ethyl group can be applied, but it is preferable to limit the number of the carbon atoms to 5 or less.

Also, the above-given substituent (Y) may be introduced with the number of 1 to 3 (or at one to three locations) on the benzene nucleus. The Ullmann-type reaction is known as a method to introduce the perfluoroalkyl group into those halogenated aromatic compounds, but the handling is extremely difficult due to difficulty in the preparation of copper powder to be used, and the reaction is significantly affected in proportion to the amount of the copper power used. Conversely, the method of the present invention is very easy in handling, and can introduce R$_f$ into the aromatic compounds with a higher yield. As the palladium-type catalyst, when PdCl$_2$ or Pd(PPh$_3$)$_2$Cl$_2$ is employed, it is ascertained that a sufficient catalytic function is presented.

When the palladium black was employed instead of PdCl$_2$, and the benzene iodide and the heptafluoro (1-methylethyl)zinc iodide let reacted with the heptafluoro (1-methyl ethyl)benzene was obtained with a yield by 53%. This fact suggests that Pd(0) which is thought to be generated from PdCl$_2$ or Pd(PPh$_2$)$_2$Cl$_2$ at the action of ultrasonic waves in the presence of Zn powder is actually acting as a catalyst. It is considered that this Pd (0) forms the following reduction-oxidation cycle, and following this cycle, R$_f$ is effectively introduced into the benzene nucleus.

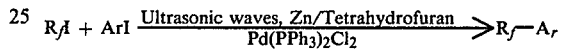

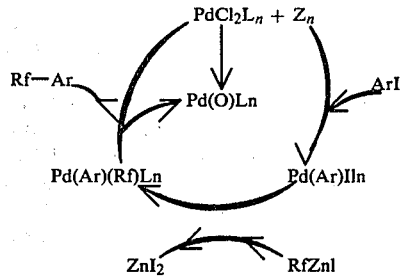

Various reactions were caused on the above-given halogenated aromatic compounds or their derivatives following the method of the present invention, and obtained the results of which the Table-3 below shows.

TABLE 3

| $R_f$ | ArI | Product*[1] | Yield (%) | Melting Point (°C.) |
|---|---|---|---|---|
| CF$_3$ | PhI | PhCF$_3$ | 82 | 101~103 |
| n-C$_3$F$_7$ | PhI | PhC$_3$F$_7{}^n$ | 78 | 127~130 |
| n-C$_4$F$_9$ | PhI | PhC$_4$F$_9{}^n$ | 81 | 82~84/48*[2] |
| i-C$_3$F$_7$ | PhI | PhC$_3$F$_7{}^i$ | 87 | 124~126 |
| i-C$_3$F$_7$ | 4-CH$_3$C$_6$H$_4$I | 4-CH$_3$C$_6$H$_4$C$_3$F$_7{}^i$ | 81 | 146~148 |
| i-C$_3$F$_7$ | 3-CH$_3$C$_6$H$_4$I | 3-CH$_3$C$_6$H$_4$C$_3$F$_7{}^i$ | 68 | 145~147 |
| i-C$_3$F$_7$ | 2-CH$_3$C$_6$H$_4$I | 2-CH$_3$C$_6$H$_4$C$_3$F$_7{}^i$ | 59 | 140~143 |

*[1]: The structure of the product was identified by IR, NMR, and mass spectrography analysis.
*[2]: Indicates a boiling point (°C./mmHg).

With this method, it is preferable that the amount of zinc powder added in the course of reaction is limited within a range of 1 to 3 times (molar ratio) that of R$_f$I. Since the initiating substances to be used are stabilized respectively, and the reaction can be carried out within a single reactor under the condition of the ambient temperature and atmospheric pressure, the method is most practicable because of an easier handling.

It is enough to use ultrasonic waves obtainable from a commercially available ultrasonic-wave cleaner, which act in the presence of zinc powder and palladium-system catalyst. Thus, the handling is made easier.

Where solvents are used for the reaction according to the method of this invention, it is preferable to employ aprotic polar solvents such as dimethylformamide, tetrahydrofuran, dimethylsulfoxide, dimethylacetamide, N-methylpyrrolidone, hexamethylphosphonamide, acetonitrile and so on. Since these polar catalysts possess a greater solvation energy against cation, they present a stronger dissolving action, and accelerate the reaction rate of anionic reagents. Further, according to the method of the present invention, where the initiating substance itself is of liquid, it is not always necessary to use the above-described solvents.

The present inventor has found out that, apart from the above-stated synthetic reaction, the desired fluorine-containing aliphatic unsaturated compound or fluorine-containing aromatic compounds can be synthesized with the following reaction in a stabilized fashion and with a good yield.

That is, as an initiating substance, a fluorine-containing aliphatic zinc iodide represented by the following formula instead of the above-given $R_fI$ is employed.

$$R_fZnI$$

(where $R_f$ is similar to the above-given one) This $R_fZnI$ is reacted in the presence of ultrasonic wave action and in the presence of a halogen-substituted aliphatic unsaturated compound or a halogen-substituted aromatic compound and a palladium-type catalyst.

Thereby, the above-mentioned $R_f$ is introduced into the above-said multiple bond or benzene nucleus, and it is possible to obtain an aliphatic unsaturated compound or aromatic compound from which the above-stated halogen is eliminated. This reaction is characterized by the employment of the $R_fZnI$ itself which is considered to be an intermediate product at the respective reaction described as above as an initiating substance.

This is represented, for instance, as follows.

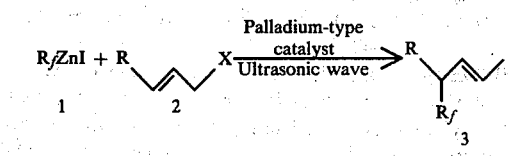

Thus, the product similar to that of the above, for instance, a fluorine-containing allyl compound derivative (3) can be obtained. The reaction conditions for palladium-system catalysts, ultrasonic waves, solvents and etc. may be similar to that of above-described one.

According to this reaction, it is characteristic to use the pre-synthesized $R_fZnI$. Even in this case, it is thought that, similar to the above description, the action of ultrasonic waves causes a closer interaction between the reacting molecules, and with the catalystic action of a palladium-type catalyst, the generation of a desired product may be accelerated. That is, it is presumed that, in particular, the bonding of $R_f$-Zn of $R_fZnI$ is made weaker due to the ultrasonic wave energy, the interaction between the reacting substances is increased, and the reaction between both of them may proceed to the full extent.

The $R_fZnI$ itself well dissolves into the solvent, thereby the reaction proceeds in a ready manner. Also, the $R_fZnI$ can be synthesized by causing the above-said $R_fI$ and Zn powder to react with each other within an autoclave, for instance, at a temperature range, 120° to 150° C. In this case, it is advisable to use an amount of Zn at one to three times (the number of mols) that of $R_fI$.

The above-described fluorine-containing compounds which are synthesized by means of the method of the present invention are useful as the synthetic intermediates for water- or oil-repellent agents, medicines and agricultural chemicals, and surface active agents, or the monomers to produce fluorine-containing polymers.

With the method of the present invention, fluorine-containing allyl derivatives represented by the following formula can be obtained. Formula:

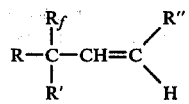

(where $R_f$ indicates the fluorine-containing aliphatic group preferably with the number of carbon atoms of 10 or less; R, R' and R" indicate the hydrogen atom, the alkyl group or alkenyl group preferably having carbon atoms of 10 or less, or aromatic group, or aromatic group substituted by the substituent.)

As the $R_f$ of this fluorine-containing allyl derivatives represented by the above Formula, the fluorine-containing aliphatic groups represented by the Formula: $CF_3(CF_2)n-$ or $(CF_3)_2CF(CF_2)n-$ can be mentioned. These include are $CF_3-$, $CF_3CF_2-$, $CF_3(CF_2)_2-$, $CF_3(CF_2)_3-$, $CF_3(CF_2)_4-$, $CF_3(CF_2)_5-$, $(CF_3)_2CF-$, $(CF_3)_2CFCF_2-$, $(CF_3)_2CF(CF_2)_2-$, $(CF_3)_2CF(CF_2)_2-$, and so on.

Apart from these alkyl groups, it is possible to use the unsaturated group, particularly the alkenyl group, for instance, $CF_2=CF-CF_2-$, $CF_3-CF=CF-$, and the like. However, it is preferable to limit the number of carbon atoms of the fluorine-containing aliphatic group 10 or less taking into account the solubility against solvents. And, as the above-described fluorine-containing aliphatic group, it is possible to use not only the above-enumerated perfluoroalkyl group or alkenyl group, but also, for instance, $CF_3(CF_2)_2CH_2CF_2-$ which is bonded with the hydrogen atoms at a part of the molecular chain. In addition, as the above-given $R_f$, other than the above, the aromatic group substituted aliphatic groups, for instance, $C_6H_5-CF_2-$, $C_6H_5-(CF_2)_2-$ and the like may be used.

Also, as the above given R, R' and R", apart from the hydrogen atoms, the alkyl group such as methyl group, ethyl group, propyl group, isopropyl group, butyl group or alkenyl groups containing partially unsaturated bond may be applied, but it is preferable to limit the number of carbon atoms to 10 or less. And, where the aromatic group substituted with the substituent is applied, it is necessary to use the substituent which will not substantially affect the proceeding of dehalogenating reaction. As those substituents, the alkyl group or alkenyl group may be used, but it is advisable to limit the number of the carbon atoms to 5 or less. Also, as the other substituents, other than the above-described alkyl group or alkenyl group, the aryl group, halogens like Cl, nitro group, cyano group and alkoxy group containing 5 or less number of the carbon atoms may be counted.

Further, the present invention proposes another method, in producing the desired fluoroketone groups, which is characterized by a process to generate the metallic halogenated ketone represented by the Formula:

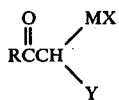

(where R represents the aliphatic hydrocarbon oxy group, aliphatic hydrocarbon group or fluoro aliphatic hydrocarbon, and includes those forming rings between the carbon atoms being bonded with X; X:halogen; Y:hydrogen or fluorine atom; M:zinc or magnesium), with the metal (M) consisting of zinc or magnesium, by causing the reaction with the halogenated ketone which is represented by the Formula:

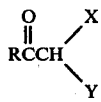

(where R, X and Y are similar to the above-given description); and with a process to generate the fluorodiketone which is represented by the Formula:

(where R and Y are similar to the previous description, and $R_f$ is fluoro-aliphatic hydrocarbon group and includes those containing ether bonds within the chain.) by causing the above-given metallic halogenated ketone to react with the fluoroester which is represented by the Formula:

(where $R_f$ is as described above, and R' is an aliphatic hydrocarbon group or aromatic hydrocarbon group.) in the presence of the action of ultrasonic waves.

That is, this method takes advantage of the strong, electrophilic property of $R_f$ under the presence of fluorine in particular within the structure of the above-given fluoroester, and by making the interaction between the fluoroester and the above-given metal halogenated ketone by means of the energy of ultrasonic waves (it is enough to use a commercially available ultrasonic cleaner), a full and easier reaction between both of them was attained. Thereby, it became possible to fluorinate the objects with the use of various fluoroesters, and the production of them was capable of being processed with a higher yield under the milder conditions. In addition, it was found out that the reaction could proceed satisfactorily by using the commercially available zinc and magnesium without refining them, contrary to the case of the conventional Reformatsky reaction.

The method of the present invention can cause the above-given halogenated ketone to react with the fluoroester by subjecting them to the action of ultrasonic waves in the presence of zinc or magnesium. It is therefore possible to obtain the desired compound by putting all the reacting reagents into a reactor from the start in the presence of action of the ultrasonic waves. Conversely, it also is able to obtain the desired product, firstly by generating the above-said metal halogenated ketone with the reaction of the above-described ketone with zinc or magnesium under the action of ultrasonic waves, then letting the ketone react with the above fluoroester under the action of ultrasonic waves. In this case, the generation of the above-described metallic halogenated ketone will not always require the action of ultrasonic waves, and it is possible to obtain the metallic halogenated ketone by causing the reaction of the halogenated ketone with zinc or magnesium under heating.

At the method of the present invention, it is preferable to let the above-stated reaction proceed within the aprotic polar solvents so as to accelerate a reaction rate. As the polar solvent, it is possible to use the tetrahydrofuran, dimethylformamide, acetonitrile, dimethylsulfoxide, dimethylacetamide, N-methylpyrolidone, hexamethylphosphoamide or mixtures of two or more of the above substances.

Secondly, for the reaction reagents to be used for the method of the present invention, it is possible to apply the aliphatic hydrocarbon-oxy group (alkoxy group such as $-OCH_3$, $-OC_2H_5$, $-OC_3H_7$, $-OC_4H_9$), aliphatic hydrocarbon group (alkyl group such as $-CH_3$, $-C_2H_5$, $-C_3H_7$, $-C_4H_9$ or alkenyl group with the number of the carbon atom similar to the former), or fluoro aliphatic hydrocarbon group (fluoroalkyl group such as $-CF_3$, $-C_2F_2$, $-C_3F_7$, $-C_4F_9$ or fluoroalkenyl group with the number of carbon atom similar to the above), all of which R is to be with the number of carbon atom at 10 or less. In addition, it is sufficient that this R may be the one which forms rings between the carbon atoms which are bonded with the above-described Y, as in the case of d-3-halogenated camphor. Also, it is preferable that X contained in the halogenated ketone is to be of the bromine atom or iodine atom.

Further, the above-described fluoroester, $R_f$ which becomes the source for introducing fluorine into the subject compound, may consist of fluoroalkyl group or alkenyl group which contains the carbon atoms in the number of 15 or less. These include: fluoroalkyl group such as $-CF_3$, $-C_2F_2$, $-C_3F_7$, $-C_4F_9$ or $-C_5F_{11}$, or fluoroalkenyl containing the similar number of the carbon atoms, also included are those fluoroalkenyl groups or alkenyl groups which are partially substituted and introduced with other halogens (i.e. Cl). Also, this $R_f$ may be the fluoroalkylether group which is represented by the following Formula, which can form an optical isomer containing the asymmetric carbon, and form a shift reagent being superior in NMR analysis (nuclear magnetic resonance analysis).

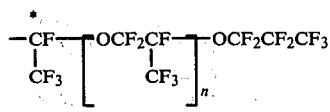

(where $n = 0 \sim 3$; $C^* =$ asymmetric carbon). And also, the R' contained in this fluoroester may consist of the above-given alkyl group or alkenyl group which contains the carbon atoms in the number of 10 or less.

Now, the above-stated method is described in a more detailed fashion.

First, the Reformatsky-type reagent (9) is generated by causing the brominated ester (8) to react with zinc powder under the action of ultrasonic waves, then by reacting this reagent (9) with the fluoroalkylester (10) under the action of ultrasonic waves, and the desired β-fluoroalkyl-β-ketocarboxylic acid ester (11) can be obtained.

$$\text{BrCHYCOOC}_2\text{H}_5 + \text{Zn} \xrightarrow[\text{Mixed solvents}]{\text{Ultrasonic wave}} \text{BrZnCHYCOOC}_2\text{H}_5$$

8     (Tetrohydrofuran:    9
dimethylformamide
= 2:1)

$$\text{BrZnCHYCOOC}_2\text{H}_5 + \text{R}_f\text{COOR}' \xrightarrow{\text{Ultrasonic wave}}$$

9      10

$$\underset{11}{\text{C}_2\text{H}_5\text{O}\overset{\text{O}}{\overset{\|}{\text{C}}}\text{CHY}\overset{\text{O}}{\overset{\|}{\text{C}}}\text{R}_f}$$

With this reaction, a R$_f$CO group could be selectively introduced into the object 11 within the similar reactor under mild conditions, and the result with a very good yield is shown on the following Table-4.

TABLE 4

| Y in 8 | R$_f$COOR'$_{10}$ | Products$_{11}$ | Yield (%) |
|---|---|---|---|
| H | CF$_3$COOC$_2$H$_5$ | C$_2$H$_5$OCOCH$_2$COCF$_3$ | 83 |
| H | C$_2$F$_5$COOC$_2$H$_5$ | C$_2$H$_5$OCOCH$_2$COC$_2$F$_5$ | 86 |
| H | ClCF$_2$COOCH$_3$ | C$_2$H$_5$OCOCH$_2$COCF$_2$Cl | 65 |
| F | CF$_3$COOC$_2$H$_5$ | C$_2$H$_5$OCOCHFCOCF$_3$ | 78 |
| F | C$_2$F$_5$COOC$_2$H$_5$ | C$_2$H$_5$OCOCHFCOC$_2$F$_5$ | 76 |
| F | ClCF$_2$COOCH$_3$ | C$_2$H$_5$OCOCHFCOCF$_2$Cl | 52 |

However, when the ordinary hydrocarbon-system RCOOR' was used instead of R$_f$COOR' at the above-described reaction, the reaction did not proceed even under the irradiation of ultrasonic waves, and the desired ketocarboxylic acid ester could not be obtained. This shows that R$_f$ of the R$_f$COOR' used for the present invention has strong electrophilic property, and that this fact contributes to the nucleophilic reaction with the Reformatsky type reagent proceeding fully.

In the meantime, at the above-described reaction, even when magnesium instead of zinc was used to react with R$_f$COOR' according to the Grignard method, it was found out that the required ketocarboxylic acid ester (11) could be obtained. It also is considered that the reaction may proceed with a high yield due to the above-given properties of R$_f$ and the action of the ultrasonic wave energy.

Also, in the above reaction, it is possible to use, for the halogenated ketone (8) to produce the reagent (9), the substance represented by the Formula:

$$\text{R}\overset{\text{O}}{\overset{\|}{\text{C}}}\text{CHYX}$$

This halogenated ketone may be the one which introduces fluorine into the object. In this case, it is enough to substitute R with the fluoroalkyl group (R$_f$).

However, when the bond between R-C of ketone is split and R is eliminated in the course of the reaction, and if fluorine (F) is adopted for the above-described Y, even when R is not present in the object, fluorine as Y can be introduced, and the physiological activity can be maintained.

Further, as this halogenated ketone, when the brominated acetone (BrCHYCOCH$_3$) of which R consists of the alkyl group is used instead of the above-described brominated ester (8), the product (11) can be obtained with a good yield. When the brominated fluoroacetone $$\text{(i.e. CF}_3\overset{\text{O}}{\overset{\|}{\text{C}}}\text{CH}_2\text{Br)}$$

which substitutes this R with the fluoroalkyl gorup (R$_f$) is used, and this substance is reacted with the fluoroester $$\text{(i.e. CF}_3\text{CF}_2\text{CF}_2\text{O}\overset{*}{\underset{\underset{\text{CF}_3}{|}}{\text{C}}}\text{F}\overset{\text{O}}{\overset{\|}{\text{C}}}\text{OR}')\text{ according to}$$

the following reaction Formula, a superior shift reagent (12) can be obtained.

$$\text{CF}_3\text{COCH}_2\text{Br} + \text{Zn} \xrightarrow[\text{Solvent}]{\text{Ultrasonic wave}} \text{BrZnCH}_2\text{COCF}_3 \quad 12$$

$$\text{BrZnCH}_2\text{COCF}_3 + \text{CF}_3\text{CF}_2\text{CF}_2\text{O}\overset{*}{\underset{\underset{\text{CF}_3}{|}}{\text{C}}}\text{FCOOR}' \xrightarrow{\text{Ultrasonic wave}}$$

$$\text{CF}_3\text{CCH}_2\overset{\text{O}}{\overset{\|}{\text{C}}}\overset{*}{\underset{\underset{\text{CF}_3}{|}}{\text{C}}}\text{FOCF}_2\text{CF}_2\text{CF}_3$$

(with the first CF$_3$ having O double bond)

Because this shift reagent has the ether bond which is bonded with the oxygen atoms between the asymmetric carbon and perfluoropropyl group (—CF$_2$CF$_2$CF$_3$), the bond is stabilized by oxygen, and even when the nucleophilic reagent may act, $$\text{R}_f(\overset{*}{\underset{\underset{\text{CF}_3}{|}}{\text{C}}}\text{FOCF}_2\text{CF}_2\text{CF}_3)$$

will not be eliminated. Also, it is possible to select various R$_f$'s as above, in particular, for the R$_f$ of the above-described fluoroester (R$_f$COOR'), the above stated $$-\overset{*}{\underset{\underset{\text{CF}_3}{|}}{\text{C}}}\text{F}-\left[\text{OCF}_2\underset{\underset{\text{CF}_3}{|}}{\text{CF}}\right]_n-\text{OCF}_2\text{CF}_2\text{CF}_3$$

(where n=0∼3) may be applied.

The following is a description of an example which introduces the R$_f$CO group into d-camphor as a shift reagent for NMR.

According to a similar process as described above, d-3-bromcamphor (13) was reacted with perfluoroalkylester (R$_f$COOR') (10) while irradiated with the ultrasonic waves, according to the following Formula in the presence of zinc powder, and the desired shift reagent (14) was obtained with ease and a high yield.

This d-camphor derivative (14) is excellent as a shift reagent, and was obtained with a high yield as shown in the following Table-5.

TABLE 5

| $R_fCOOR'$ | Product 14 | Yield (%) |
|---|---|---|
| $CF_3COOC_2H_5$ | (camphor derivative with $COCF_3$) | 86 |
| $C_2F_5COOC_2H_5$ | (camphor derivative with $COC_2F_5$) | 84 |
| $C_3F_7COOC_2H_5$ | (camphor derivative with $COC_3F_7$) | 76 |
| $ClCF_2COOCH_3$ | (camphor derivative with $COCF_2Cl$) | 61 |
| $CH_2=CHCH_2\underset{CH_2CH=CH_2}{\overset{CF_3}{\underset{|}{C}}}CO-\underset{FO}{\overset{|}{}}$ | (camphor derivative with $COC(CF_3)(F)(CH_2CH=CH_2)$) | 51 |

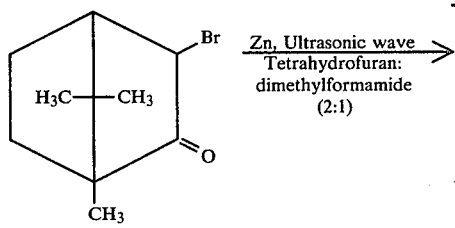

13

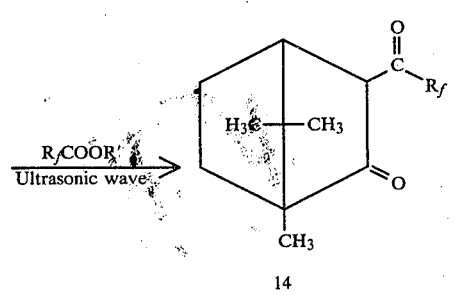

14

As described above, the method of this invention utilizes the chemical properties of the fluoroaliphatic hydrocarbon group ($R_f$) and the action of ultrasonic wave in combination, so that several remarkable effects, which can not be expected by the conventional method, can be obtained. Particularly, since the reaction can proceed under the mild condition without being accompanied by severe reaction, the handling is easy, and the various fluoroesters ($R_fCOOR'$) to be used can be selected without any restriction. Also, even when the commercial zinc powder or magnesium powder is used without refining, it has full activity, and further, the commercially available solvents may be well used with only drying them by means of a molecular sieve, for instance, without refining.

The fluoro-β-diketone which can be obtained by the method of this invention are characterized being represented by the following Formula:

$$\underset{\text{RCCHYCR}_f}{\overset{\text{O O}}{\underset{\|\;\;\|}{}}}$$

(where R represents a fluorohydrocarbon group, and fluorohydrocarbon group or hydrocarbon group which have ether bonds in their chain such as

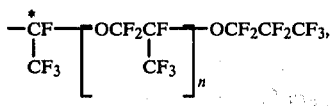

including those forming rings between the carbon atoms which are bonded with Y, Y is hydrogen atom or fluorine atom, $R_f$ represents a fluorohydro-carbon group, and includes those having ether bonds in their chains (i.e. the ether bond similar to that of the above-given R.)).

The compounds among these fluoro-β-diketones in which the asymmetric carbon C is present are effective to form a chiral shift reagent such as europium chelates. That is, due to the fluorine atoms, (1) the electrophilic property is strengthened, and the chelate is activated, resulting in the increase of the Lewis acidity as the shift reagent, whereby an excellent shift effect is obtained even at a lower concentration.

(2) As presence of the hydrogen atoms which overlap the substrate lessens, the overlapping with the signal of the substrate becomes decreased.

(3) The solubility against the organic solvents is increased.

(4) When the R in the above-given Formula is

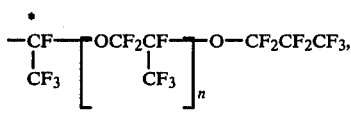

it becomes a symmetric structure from the viewpoint of the molecular structure, and the shift reagent is stabilized due to the steric effect, and it is possible to have two asymmetric centers (carbon).

In addition, these fluoro-β-diketone groups are expected to present the above-described action of the fluorine compounds due to the presence of fluorine.

Further, structurally, when R and/or $R_f$ in the above Formula is of a fluoroalkyl group which is represented by the Formula:

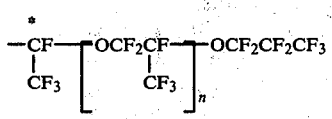

(where n=0~3), the ether bond, due to O between fluoroalkyl groups, contributes to stabilize that structure. That is, when there is no such ether bond, and the fluoroalkyl group is directly bonded to the above-given $$\overset{\text{O}}{\underset{\|}{\text{C,}}}$$

and $$\underset{\text{RCCHYCR}_f}{\overset{\text{O O}}{\underset{\|\;\;\|}{}}}$$

(for $R_f$: 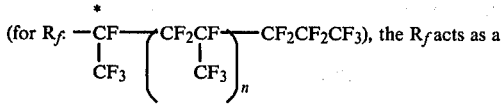), the $R_f$ acts as a pseudo-halogen, and is easily eliminated due to the action of the nucleophilic reagent onto $$\overset{\text{O}}{\underset{\|}{\text{C,}}}$$

but because of the above-stated ether bond, such chemical change is prevented, which enables maintaining the fluoroalkyl group within the molecule is a stabilized fashion.

At the above Formula, the R may be of a fluoroalkyl group or alkyl group comprising the carbon atoms with the number of 7 or less, such as $-CF_3$, $-C_3F_7$, $-C_4F_9$, or $-CH_3$, $-C_2H_5$, $-C_3H_7$, $-C_4H_9$ respectively. And also, this R may be of those forming the rings between the carbon atoms which are bonded with the above-given Y as in the case of d-camphor. These fluoro corpora of d-camphor also are useful as a shift reagent for NMR.

Now, the above-described fluoro-β-diketones are exemplified in a concrete manner according to the production processes which are different from the method of the present invention.

The perfluoro carbonic acid, for instance, perfluoro-2-peroxypropionic acid fluoride

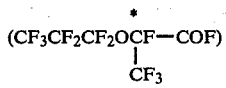

is obtained by means of the dimerization reaction of hexafluoro-1, 2-epoxypropane. This perfluoro carbonic acid fluoride (15) generates a diastereomer mixture by condensing together with (−)-α-phenylethylamine (16) according to the following Formula. Thus, the product which is obtained by separating the above-said mixture by means of column gas chromatography is hydrolyzed, and optically resolved to optically active perfluoro carboxylic acid (15′)

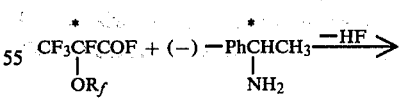

15

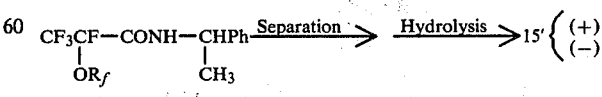

Further, at this perfluoro carboxylic acid (15′), when a perfluoroisopropyl group is applied as the above-described $R_f$, it is known that the 15' can be optically resolved in an extremely effective fashion from the mixture 16'. Among them, it is advisable to obtain perfluoro-2-isopropoxypropionic acid through fluoride (17) which is synthesized according to the following Formula.

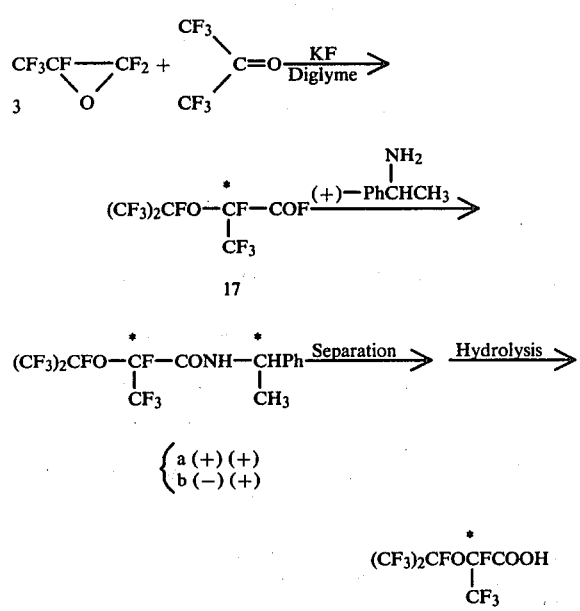

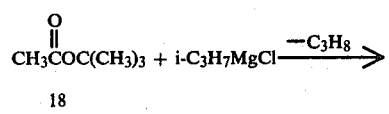

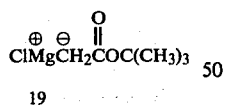

On the other hand, the enolate anion (19) which is obtained from the tert-butyl acetate (18) in accordance with the following Formula is known to be a useful reagent to obtain the corresponding β-diketone from carboxylic acid chloride.

Thus, (+)-perfluoro-2-propoxypropionic acid (15), for instance, among the above-given perfluoro carboxylic acid which was optically resolved, was converted to its acid chloride;

$$(+)\text{—}CF_3CF_2CF_2O\overset{*}{C}FCOCl$$
$$\mid$$
$$CF_3$$

(20) with phosphorus pentachloride, which was caused to react with the following Formula; thereby the desired chiral β-diketone-di(perfluoro-2-propoxypropionyl)-methane (21) was synthesized. It is possible to obtain this diketone (21) with a good yield (i.e. 90%).

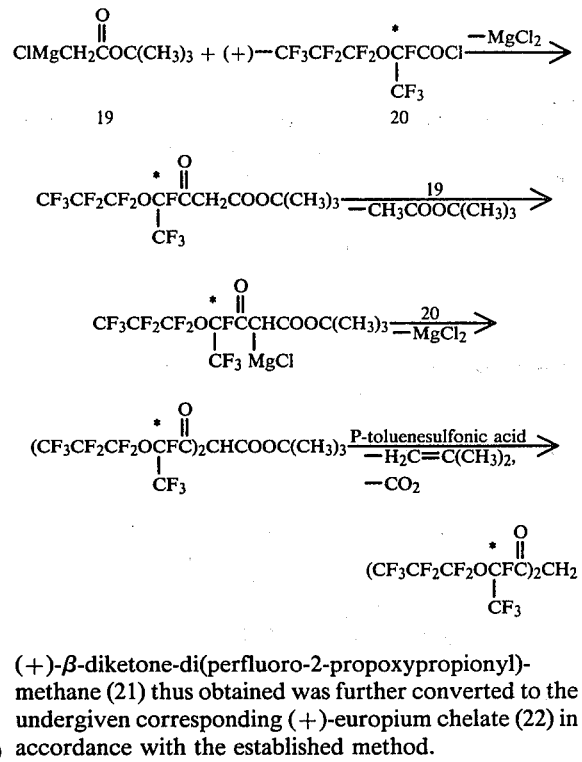

(+)-β-diketone-di(perfluoro-2-propoxypropionyl)-methane (21) thus obtained was further converted to the undergiven corresponding (+)-europium chelate (22) in accordance with the established method.

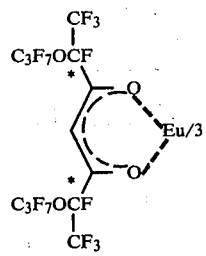

The following Table-6 shows the results examined on 1H NMR of several substrates by adding this europium chelate (22).

TABLE 6

| Substrate | Mole ratio (22/Substrate) | Signal Position | ΔΔδ (ppm) |
|---|---|---|---|
| PhCH(CH₃)NH₂ | 0.11 | CH₃ | 0.20 |
| PhCH(CH₃)OH | 0.13 | CH₃ | 0.08 |
| CH₃CH₂CH(CH₃)*COCH₃ | 0.16 | CH₃* | 0.08 |
| PhSOCH₃ | 0.10 | CH₃ | 0.08 |

According to these results, despite the fact that the europium chelate (22) as a shift reagent is extremely low in its concentration, a satisfactory ΔΔδ value (a magnitude of shift difference between enantiomers) is obtained, whereby it can be ascertained that the europium chelate (22) presents a superior shift effect. Conversely, where the publicly known tris-(3-heptafluorobutyryl-d-campharate) europium (III) is added as a shift reagent, and where α-phenylethylamine is adopted as a substrate, ΔΔδ=0.17 ppm can be obtained only when a mole ratio between a shift reagent and a substrate is raised to a high concentration of 0.40 to 0.60. This fact means that the shift reagent which uses fluoro-β-diketone is sufficient at a concentration less than the public known by ¼ to 1/6, and fully indicates a superiority of this invention.

Also, since the above-given shift reagent (22) contained no hydrogen atoms which will overlap the substrate, it was found out that a very neat ¹H NMR spectrum could be obtained. In addition, this shift reagent can dissolve into nonpolar organic solvents like carbon tetrachloride, specifically, it dissolves unlimitedly into the fluorine-system solvent such as 1,1,2-trichlorotrifluoroethane, and it can be maintained in a stabilized fashion within the given solution. Thus, where the NMR analysis is conducted, the above-described shift reagent can be added in the form of 1,1,2-trichloro-trifluoroethane solution by means of a microsyringe and the like.

Further, the above-described europium chelate (22) has not only the above-mentioned conspicuous advantages, but also a pair of perfluoroproxyethyl groups

which have asymmetric carbon atoms which are respectively positioned symmetrically. Accordingly, due to its steric effect, the molecular structure is kept stabilized, and also since it has two asymmetric centers, it presents a superior shift effect. This europium chelate generally acts to shift the spectrum toward the lower magnetic field side as a shift reagent during the NMR analysis. Contrary to that intrinsic characteristic, it is possible to form praseodymium chelate which places Pr (praseodymium) as the central atom of chelate instead of the above-given Eu so as to shift the spectrum the higher magnetic field side. In addition, the above-described substance (21) can be obtained with a good yield by means of the method of the present invention. Also, the above-given shift reagent (14) forms the chiral reagent as shown by the following Formula:

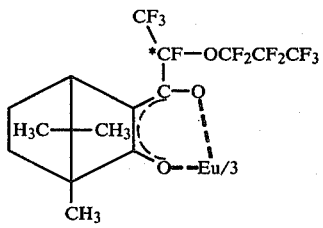

Further, here are given more detailed description in the examples which were experimented for the present invention. The under-described examples, however, do not limit the present invention, and they may be modified based on its technical concept.

EXAMPLE 1

Commercially available zinc powder (0.02 gr atom), trifluoromethyl iodide 2.15 gr (11 mmol), benzaldehyde 1.06 gr (10 mmol), and dimethylformamide 25 ml which is dried by means of a molecular sieve, were put into an eggplant-formed flask (capacity: 50 ml), and they were caused to react for 30 minutes within a water bath in the presence of the action of ultrasonic waves by means of a commercially available ultrasonic cleaner (35W, 32 kHz).

Upon completion of the reaction, and the solution was hydrolyzed by adding 100 ml of 2% hydrochloric acid, and an oil layer was extracted by means of diethylether. Then, after drying this liquid thus extracted with magnesium sulfate, the solvent was removed by means of fractional distillation. Through vacuum distillation of the residue, phenyltrifluoromethylcarbiol

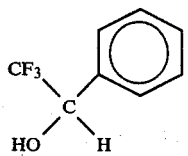

was obtained with a yield by 72% (1.27 gr).

The boiling point of this carbinol was ascertained to be at 105°~108° C./16 mmHg.

EXAMPLE 2

In Example 1, tetrahydrofuran (25 ml) was used as the solvent, and let solution underwent reaction under the conditions identical to the Example 1, phenyltrifluoromethycarbinol was obtained with a yield by 56% (0.99 gr).

EXAMPLE 3

Commercially available zinc powder 1.30 gr (0.02 gr atom), trifuluoromethyl iodide 2.15 gr (11 mmol), acetophenone 1.20 gr (10 mmol), and dimethylformamide 25 ml were put into an eggplant-formed flask (capacity: 50 ml) respectively, and they were reacted for one hour within a water bath in the presence of the action of ultrasonic waves by means of a commercially available ultrasonic cleaner (35W, 32 KHz). Upon completion of the reaction, 2% hydrochloric acid (100 ml) was added, and an oil layer was extracted by means of diethylether. After drying this extracted liquid with magnesium sulfate, the solvent was removed through fractional distillation. Through vacuum distillation of the residue, methylphenyltrifluoromethylcarbinol

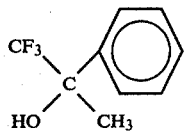

was obtained with a yield by 55% (1.25 gr).

The boiling point of this carbinol was ascertained to be at 81° to 83° C./3 mmHg.

EXAMPLE 4

Tetrahydrofuran (25 ml) was used as the solvent, and the solution was caused to react under the conditions identical to the Example 3, and methylphenyltrifluoromethylcarbinol was obtained with a yield by 43% (0.82 gr).

EXAMPLES 5 TO 9

In Example 1, for the carbonyl compounds to be used, the following compounds were respectively substituted:

C₅H₁₁CHO (Example 5),
CH₃CH=CHCHO (Example 6),
C₆H₅—CH=CHCHO (Example 7),

-continued

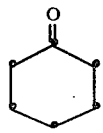 (Example 8), $CH_2=CHCOCH_2CH_3$ (Example 9), and the solution was caused to react under the conditions identical to that of the Example 1, and varied types of carbinols as shown on the following Table-7 were obtained, respectively. Further, the structure of each carbinol, including those of the Example 1 and 2, was identified by means of IR and NMR spectrography analysis.

EXAMPLE 10 TO 17

In Example 1, as the fluorine-containing aliphatic iodide and carbonyl compound, those indicated in the following Table-8 were used respectively, and the solution was reacted under the conditions identical to those of the Example 1. The amounts used were; fluorine-containing aliphatic iodide: 11 mmol, carbonyl compound: 10 mmol, respectively.

For instance, where $(CF_3)_2CFI$ was used, the amount thereof was set at 3.26 gr (11 mmol) and phenyl (heptafluoro-1-methylethyl) carbinol was obtained by making the reaction product undergo the vacuum distillation, with a yield by 54% (1.49 gr). And the boiling point thereof was ascertained at 120° to 123° C./104 mmHg. For each example, the characteristics of the the reaction substances and carbinol generated are summarized in the following Table-8.

TABLE-7

| Example | RCOR' | Reaction Time (hr) | Carbinol Chemical Structure | Yield (%) | Boiling Point (°C./mmHg) | NHR CF3 (δ) |
|---|---|---|---|---|---|---|
| 1 | $C_6H_5CHO$ | 0.5 | $CF_3$, $C_6H_5$, HO, H on central C | 72 | 105~108/16 | −0.3* |
| 3 | $C_6H_5COCH_3$ | 1.0 | $CF_3$, $C_6H_5$, HO, $CH_3$ on central C | 55 | 81~83/3 | −0.1 |
| 5 | $C_5H_{11}CHO$ | 0.5 | $CF_3$, $C_5H_{11}$, HO, H on central C | 61 | 96~97/18 | 0.6 |
| 6 | $CH_3CH=CHCHO$ | 0.5 | $CF_3$, $CH=CH-CH_3$, HO, H on central C | 62 | 92~95/105 | 0.7 |
| 7 | $C_6H_5CH=CHCHO$ | 0.5 | $CF_3$, $CH=CH-C_6H_5$, HO, H on central C | 68 | 86~88/5 | 0.4 |
| 8 | cyclohexanone | 1.5 | $CF_3$, HO on cyclohexyl C | 48 | 93~95/24 | −1.3 |
| 9 | $CH_2=CH-CO-CH_2-CH_3$ (structure shown) | 1.0 | $CF_3$, OH, $CH_2=CH-CH_2-$, $CH_3$ on central C | 45 | 94~97/65 | 3.2 |

*$^{19}F(CCl_4)$: δ−0.3 ($CF_3$, d, $JCF_3-H$ = 5.6Hz), $CF_3COOH$ to be the External Standard.
$^1H(CCl_4)$: τ5.00 (CH, q), 6.22 (OH), 7.50 (Ar—H).

TABLE-8

| Example | RCOR' | R_fI | Carbinol Chemical Structure | Yield (%) | Boiling Point (°C./mmHg) |
|---|---|---|---|---|---|
| 10 | C₆H₅CHO | (CF₃)₂CFI | (CF₃)₂CF–C(OH)(H)–C₆H₅ | 54 | 120~123/104 |
| 11 | C₄H₉CHO | (CF₃)₂CFI | (CF₃)₂CF–C(OH)(H)–C₄H₉ | 52 | 80~83/120 |
| 12 | C₆H₅COCH₃ | (CF₃)₂CFI | (CF₃)₂CF–C(OH)(CH₃)–C₆H₅ | 33 | 115~118/58 |
| 13 | C₆H₅CHO | CF₃(CF₂)₂I | CF₃(CF₂)₂–C(OH)(H)–C₆H₅ | 62 | 86~88/15 |
| 14 | C₄H₉CHO | CF₃(CF₂)₂I | CF₃(CF₂)₂–C(OH)(H)–C₄H₉ | 48 | 96~97/137 |
| 15 | C₆H₅COCH₃ | CF₃(CF₂)₂I | CF₃(CF₂)₂–C(OH)(CH₃)–C₆H₅ | 26 | 111~113/50 |
| 16 | C₆H₅CHO | CF₃(CF₂)₃I | CF₃(CF₂)₃–C(OH)(H)–C₆H₅ | 85 | 113/46 |
| 17 | C₆H₅CHO | CF₃(CF₂)₅I | CF₃(CF₂)₅–C(OH)(H)–C₆H₅ | 76 | 86~88/26 |

EXAMPLE 18

In Example 1, tin chloride (SnCl₂) was used instead of zinc powder, and the solution was reacted in the presence of the ultrasonic waves, and the conditions were identical to those of the Example 1, thereby the reaction product was hydrolyzed, and the similar phenyltrifluoromethylcarbinol was obtained.

REFERENCE EXAMPLE 19

In Example 18, instead of the action of ultrasonic waves, pyridine (5 ml) was added, and the solution was reacted under the conditions identical to those of the Example 18, thereby the reaction product was hydrolyzed, and the similar phenyltrifluoromethylcarbinol was obtained.

COMPARATIVE EXAMPLE

For comparison, in Example 1, magnesium powder was used instead of zinc powder, and the solution was reacted under conditions identical to those of the Example 1. It was ascertained that the desired fluorine-containing carbinol was not generated entirely. This similar result was confirmed where lithium powder was used.

EXAMPLE 20

By putting trifluoromethyl and zinc powder into an autoclave respectively by the specified amount, and causing them to react under heating at 120° to 150° C., CF$_3$ZnI was obtained.

This substance was put into a flask togehter with benzaldehyde and dimethyl formamide, as in the case of Example 1, and subjected to the action of ultrasonic waves within a water bath. Upon completion of the reaction; 2% hydrochloric acid (100 ml) was added, and an oil layer thus obtained was extracted, and after drying, it was subjected to the vacuum distillation, whereby the phenyltrifluoromethylcarbinol was obtained similar to that of the Example 1.

Further, where R$_f$ZnI other than the above-given CF$_3$ZnI was used, the corresponding carbinols were obtained respectively.

EXAMPLE 21

In Example 20, by using tin chloride instead of zinc powder, trifluoromethyl was caused to react with trifluoromethyl iodide (SnCl$_2$), as in the case of the Example 20, and CF$_3$SnCl$_2$I was obtained. Consecutively, as in the case of the Example 20, CF$_3$SnCl$_2$I was put into a flask together with benzaldehyde and dimethylformamide, and subjected to reaction under the action of ultrasonic waves, and the product extracted from an oil layer generated was hydrolyzed, thereby phenyltrifluoromethylcarbinol was obtained.

REFERENCE EXAMPLE 2

In Example 21, instead of ultrasonic waves, the condition where pyridine (5 ml) was used, the object was caused to react, and the reacted product was hydrolyzed, thereby the similar phenyltrifluoromethylcarbinol was obtained.

EXAMPLE 22

Commercially available zinc powder 1.3 gr (0.02 gr atom), trifluoromethyl iodide 2.15 gr (11 mmol), cinnamylbromide 1.97 gr (10 mmol) and palladium acetate 0.11 gr (0.5 mmol) were put into a flask together with tetrahydrofuran 25 ml. Then, within a water bath, these substances were subjected to reaction for a period of one hour under the action of ultrasonic waves by means of a commercially available ultrasonic cleaner (35W, 32 kHz). Then, the solution within the flask was poured into the water, whereby an oil layer was further extracted by means of diethylether. After drying this extracted liquid with magnesium sulfate, the solvent was removed by means of fractional distillation.

By distillating residues, 3-trifluoromethyl-3-phenyl-1-propene (ph(CF$_3$)CHCH=CH$_2$)having a boiling point of 81° to 85° C./25 mmHg was obtained with a yield by 63%. The spectrum analysis value of this product was:
Mass: M+ 186.
IR: 1220 cm$^{-1}$ (C-F).

EXAMPLE 23

In Example 22, zinc powder 1.30 gr (0.02 gr atom), trifluoromethyl iodide 2.35 gr (12 mmol), trans-β-bromostyrene 1.83 gr (10 mmol), and tetrakis (triphenylphosphine) palladium 0.23 gr (0.2 mmol) were used, and subjected to the reaction as in the case of the Example 22 within tetrahydrofuran (25 ml). When the product was treated as in the case of the Example 22, and after distillation, trans-β-trifluoromethylstyrene (PhCH=CHCF$_3$) with a boiling point of 70° to 72° C./25 mmHg was obtained with a yield by 65%. The spectrum analysis values of this product were:
Mass: M+ 172.
IR: 1215 Cm$^{-1}$ (C-F).

EXAMPLE 24

In Example 22, zinc powder 1.30 gr (0.02 gr atom), benzene iodide 2.04 gr (10 mmol), heptafluoro-1-methylethyl iodide 2.26 gr (11 mmol), and bis(triphenylphospine) palladium dichloride 0.07 gr (0.01 mmol) were used, and subjected to the reaction for 30 minutes within tetrahydrofuran (25 ml) under the action of ultrasonic waves. Then, by treating the product similarly to the Example 22, and by means of distillation, heptafluoro-1-methylethyl benzene

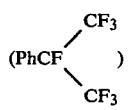

with a boiling point of 124° to 126° C. was obtained with a yield by 87%.
The spectrum analysis values were:
Mass: M+ 246.
IR: 1130 to 1310 Cm$^{-1}$ (C-F).

EXAMPLE 25

In Example 22, zinc powder 1.30 gr (0.02 gr atom), trifluoromethyl iodide 2.35 gr (12 mmol), 1-tolyl-3-bromo-1-propene 2.11 gr (10 mmol), and palladium acetate 0.11 gr (0.5 mmol) were subjected to the reaction similar to that of the Example 22 within tetrahydrofuran 25 ml.

The product was treated as in the case of the Example 22, after distillation, 3-trifluoromethyl-3-tolyl-1-propene (4-CH$_3$C$_6$H$_4$(CF$_3$) CHCH=CH$_2$) with a boiling point of 90° to 92° C./26 mmHg was obtained with a yield by 67%.
The spectrum analysis values were:
Mass: M+ 200.
IR: 1215 Cm$^{-1}$ (C-F).

EXAMPLE 26

In Example 22, zinc powder 1.30 gr (0.02 gr atom), trifluoromethyl iodide 2.15 gr (11 mmol), 1-bromo-2-tolyl ethene 1.97 gr (10 mmol), and tetrakis(triphenylphosphine) palladium 0.23 gr (0.2 mmol) were used and subjected to the reaction within tetrahydrofuran (25 ml) as in the case of the Example 22. The product was treated similarly to the Example 22, and was recrystallized by means of petroleum ether, thereby 1-trifluoromethyl-2-tolyl-ethene 4-CH$_3$C$_6$H$_4$CH=CHCF$_3$ with a melting point of 59° to 60° C. was obtained with a yield by 67%. The spectrum analysis values of this product were:
Mass: M+ 186.
IR: 1210 Cm$^{-1}$ (C-F).

EXAMPLE 27

In Example 22, zinc powder 1.30 gr (0.02 gr atom), heptafluoro-1-methylethyl iodide 2.26 gr (11 mmol) cinnamylbromide 1.97 gr (10 mmol), and palladium acetate 0.11 gr (0.5 mmol) were used and subjected to the reaction within tetrahydrofuran (25 ml) as in the case of the Example 22. When the product was treated similarly to the Example 22, 3-phenyl-3-(heptafluoro-1-methylethyl)-1-propene (Ph($C_3F_7$)CHCH=$CH_2$) with a boiling point of 80° to 82° C./21 mmHg was obtained with a yield by 78%. The spectrum analysis values were:

Mass: $M^+$ 286.
IR: 1120 to 1310 $Cm^{-1}$ (C-F).

EXAMPLE 28

By putting the specified amount of trifluoro-methyl iodide and zinc powder respectively into an autoclave, and subjecting them to the reaction while heated at 120° to 150° C., trifluoromethyl zinc iodide ($CF_3ZnI$) was obtained. This $CF_3ZnI$ was put into a flask together with cinnamylbromide palladium diacetate and tetrahydrofuran, as in the case of the Example 22, and was subjected to the reaction under the action of ultrasonic waves. When the solution thus obtained was treated similarly to the Example 22, after distillation, 3-trifluoromethyl-3-phenyl-1-propene similar to that of the Example 22 was obtained.

EXAMPLE 29

(1) Synthesis of $CF_3COCH_2COCF_3$ $CF_3COCH_2Br$ (1.91 gr, 10 mmol), $CF_3CO_2C_2H_5$ (1.42 gr, 10 mmol), and zinc powder (1.3 gr) were put into a flask (100 ml) together with a mixed solvent comprising tetrahydrofuran (20 ml) and dimethylformamide (10 ml), and they were subjected to the reaction for a period of one hour while being irradiated with ultrasonic waves by means of an ultrasonic cleaner (35W, 32 kHz). After the reaction, impurities contained in the mixed liquid were filtered, then water (500 ml) was added to the filtered liquid, whereby an oil layer generated was extracted by means of diethylether. After drying the extracted liquid with magnesium sulfate, the solvent was removed. The product ($CF_3COCH_2COCF_3$) (bp: 70° to 72° C.) was obtained through distillation with a yield by 69%.

(2) Synthesis of $CF_3COCH_2COCF(CF_3)OCF_2CF_2CF_3$ $CF_3COCH_2Br$ (1.91 gr, 10 mmol), $CF_3CF_2CF_2OCF(CF_3)CO_2C_2H_5$ (3.58 gr, 10 mmol), and zinc powder (1.3 gr) were put into a flask (100 ml) together with a mixed solvent comprising tetrahydrofuran (20 ml) and dimethylformamide (10 ml), and they were subjected to the reaction for a period of one hour under the action of ultrasonic waves by means of an ultrasonic cleaner (35W, 32 kHz). After the reaction, impurities within the mixed solution were filtered, and to the filtered liquid there was added water (500 ml), and an oil layer thus generated was extracted with diethylether. After drying the extracted liquid with magnesium sulfate, the solvent was removed through fractional distillation. The product (bp: 80° to 83° C./150 mmHg) was obtained by means of distillation with a yield of 58%. The spectrum analysis values were:

Mass: $M^+$ 440.
NMR: $^1H$ ($\delta$) ($CDCl_3$), 5.2($CH_2$) ppm, $^{19}F$ ($\delta$), −11($CF_3CO$), 1.6(1F), 4.2(3F), 4.8(3F), 6.6(1F), 52(2F), 58(1F)ppm (External Standard: $CF_3CO_2H$).

EXAMPLE 30

(1) Synthesis of $C_2H_5OCOCH_2COCF_3$ $BrCH_2CO_2CH_2CH_3$ (1.67 gr, 10 mmol), $CF_3CO_2CH_2CH_3$ (1.42 gr, 10 mmol), and zinc powder (1.3 gr) were put into a flask (100 ml) together with a mixed solvent comprising tetrahydrofuran (20 ml) and dimethylformamide (10 ml), and they were subjected to the reaction for a period of one hour under the irradiation of ultrasonic waves by means of an ultrasonic cleaner (35W, 32 kHz). After the reaction, impurities contained in the mixed liquid were filtered, and water (500 ml) was added to the filtered liquid. An oil layer thus generated was extracted with diethylether. After drying the extracted liquid with magnesium sulfate, the solvent was removed through fractional distillation. The product (bp: 70° to 72° C./102 mmHg) was obtained by means of the vacuum distillation with a yield by 83%.

(2) Synthesis of $C_2H_5OCOCHFCOCF_3$

Ethyl bromofluoroacetate ($BrCHFCO_2C_2H_5$; 1.85 gr, 10 mmol), $CF_3COOC_2H_5$ (1.42 gr, 10 mmol), and zinc powder (1.3 gr) were put into a flask (100 ml) together with a mixed solvent comprising tetrahydrofuran (20 ml) and dimethylformamide (10 ml), and subjected to the reaction for a period of one hour while being irradiated with ultrasonic waves by means of an ultrasonic cleaner (35W, 32 kHz). After the reaction, impurities contained in the mixed liquid were filtered, and water was added to the filtered liquid, and an oil layer thus generated was extracted with diethylether. After drying the extracted liquid by means of magnesium sulfate, the solvent was removed through fractional distillation. Then the product (bp: 72° to 74° C./96 mmHg) was obtained by means of the vacuum distillation. The spectrum analysis values were:

Mass: $M^+$ 202.
NMR: $^1H$ ($\delta$) ($CDCl_3$), 1.0 ($CH_3CH_2$), 2.3 ($CH_3CH_2$), 4.6 (CH) ppm $^{19}F$ ($\delta$), −13($CF_3$), +116 (CF) ppm (External Standard: $CF_3CO_2H$).

EXAMPLE 31

(1) Synthesis of $C_2H_5OCOCH_2COC_2F_5$ $BrCH_2CO_2C_2H_5$ (1.67 gr, 10 mmol), $C_2F_5CO_2C_2H_5$ (1.92 gr, 10 mmol), and zinc powder (1.3 gr) were put into a flask (100 ml) together with a mixed solvent comprising tetrahydrofuran (20 ml) and dimethylformamide (10 ml) and treated similarly to the Example 30, and the product (bp: 83° to 85° C./91 mmHg) was obtained by means of the vacuum distillation with a yield by 86%. The spectrum analysis values were:

Mass: $M^+$ 234.
NMR: $^1H$ ($\delta$)($CDCl_3$) 1.1 ($CH_3CH_2$), 2.2 ($CH_3CH_2$), 4.1 ($CH_2$)ppm $^{19}F$ ($\delta$) 1.6 ($CF_3$) 29 ($CF_2$)ppm (External Standard: $CF_3CO_2H$).

(2) Synthesis of $C_2H_5OCOCHFCOC_2F_5$

As in Example 1, by using $BrCHFCOOCH_2CH_3$ (1.85 gr, 10 mmol), $C_2F_5CO_2C_2H_5$ (1.92 gr, 10 mmol), and zinc powder (1.3 gr), and tetrahydrofuran (20 ml) and dimethylformamide (10 ml), as the solvents, a treatment similar to that of Para (1) was conducted. Through the vacuum distillation, the product (bp: 78°~80° C./80 mmHg) was obtained with a yield by 74%.

The spectrum analysis values were:

Mass: M+ 252.
NMR: $^1$H ($\delta$) (CDCl$_3$), 1.1 (CH$_3$CH$_2$) 2.1 (CH$_3$C$\underline{H}_2$), 4.5 (CH) ppm $^{19}$F ($\delta$) 1.4 (CF$_3$), $\overline{32}$ (CF$_2$), 114 (CF) ppm (External Standard: CF$_3$CO$_2$H).

EXAMPLE 32

Synthesis of

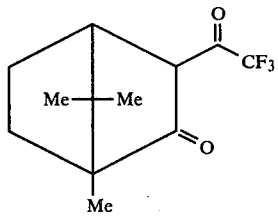

(1) d-3-bromcamphor (4.62 gr, 10 mmol), CF$_3$COOC$_2$H$_5$.

(3.1 gr, 22 mmol), and magnesium (0.53 gr) were mixed with diethylether (30 ml), and put into a flask (100 ml), and they were subjected to the reaction for a period of 40 minutes while being irradiated with ultrasonic waves by means of an ultrasonic cleaner (35W, 32 kHz). After the reaction impurities contained in the mixed liquid were filtered, and 2% HCl water solution (500 ml) was added, and an oil layer thus generated was extracted with diethylether. After cleaning the extracted liquid with saturated water solution (NaHCO$_3$), it was dried with magnesium sulfate.

After removal of the solvent by means of fractional distillation, the product (bp: 76° to 80° C./5 mmHg) was obtained through the vacuum distillation with a yield by 94%. The spectrum analysis values of this product were:

NMR: $^1$H($\delta$)(CCl$_4$), 0.85 (3H) 1.0 (6H), 1.2~2.3 (5H), 2.85 (1H)ppm $^{19}$F($\delta$) −24 (CF$_3$)ppm (External Standard: CF$_3$CO$_2$H).

(2) As in the reaction of the above Para (1), d-3-bromcamphor (4.62 gr, 20 mmol), CF$_3$COOC$_2$H$_5$ (3.1 gr, 22 mmol), and zinc powder (2.6 gr) were mixed with tetrahydrofuran (30 ml), and put into a flask (100 ml), then they were subjected to the reaction for a period of one hour under the action of ultrasonic waves by means of an ultrasonic cleaner (35W, 32 kHz). After the reaction, impurities contained in the mixed liquid were filtered, and the water (500 ml) was added to the filtered liquid, and an oil layer was extracted with diethylether. After drying with magnesium sulfate, the solvent was removed by means of fractional distillation, thence the product was obtained through the vacuum distillation with a yield by 86%.

REFERENCE EXAMPLE 3

(1) Synthesis of optically active perfluoro-2-propoxypropionic acid

Perfluoro-2-propoxypropionic acid fluoride (13.28 gr, 40 mmol) was inserted, within the water bath, into a dichloromethane solution (50 ml) containing (−)-α-phenylethylamine (48.4 gr, 40 mmol) and triethylamine (4.04 gr, 40 mmol). After inserting the mixture was further stirred for a period of 30 minutes under the room temperature. The mixture reacted was cleaned with water and 1 normal hydrochloric acid, and after drying, the solvent was removed, whereby the oily diastereomer mixture ((+)-(−) and (−)-(−)) was obtained. This mixture was separated by means of the mixed solvent comprising hexane and benzene (3:1) within a silica gel column. (−)-(−) amide (6.23 gr, 72%) was obtained as the first fraction. This amide was ascertained to have a melting point, 55.5° to 56.5° C., $[\alpha]_D^{20}$ −82.0° (c1.00, C$_6$H$_6$). And as the second fraction, 6.06 gr (70%) of (+)-(−) amide with a melting point, 83° to 83.5° C., $[\alpha]_D^{20}$ −88.0° (c 1.00, C$_6$H$_6$) was obtained.

Both of them, at the IR spectrum, presented the characteristic absorption of NH and C=O at 3300 Cm$^{-1}$ and 1700 Cm$^{-1}$ respectively. Also at $^1$H NMR (in CCl$_4$), both of them presented the entirely identical patterns; ($\delta$ 1.53 (Me), 5.12 (CH), 6.72(NH), 7.27(Ph)). However, for $^{19}$F NMR, at the chemical shift of the terminal trifluoromethyl group of perfluoropropoxy group, it was found out that (−)-(−) amide was presented at the lower magnetic field of 9 Hz compared with (+)-(−) amide. Also, at the gas chromatography, both of them were different in their retention time, and the purity could be determined by means of $^{19}$F NMR and gas chromatography.

The pure (+)-(−) amide 4.33 gr (10 mmol) was added into the solvent (40 ml) which was a mixture of water and ethanol containing 10% of sodium hyroxide, and subjected to heating and reflux for a period of 16 hours. The reaction liquid was neutralized with hydrochloric acid, and carboxylic acid thus generated was extracted by means of ether. After drying the extracted liquid with magnesium sulfate, ether was removed, and by subjecting the residue to the vacuum distillation, (+)-perfluoro-2-propoxypropionic acid (2.28 gr, 69%) was obtained. ($\alpha_D^{28}$+26.50° (neat, l=1)).

Similarly, from (−)-(−) amide, (−)-perfluoro-2-propoxypropionic acid (2.38 gr, 72%) was obtained. ($\alpha_D^{28}$−26.30° (neat, l=1)).

The material-property values, IR, and NMR spectrum values of both of them are given as follows:
Boiling point: 93°~94° C./90 mmHg.
IR (film): 3200 (OH), 1780 (C=O)cm$^{-1}$.
$^1$H NMR (CDCl$_3$): $\delta$10.3 ppm.
$^{19}$F NMR (neat): $\delta$2.7 (1F), 5.43 (3F), 6.3 (3F), 10.0 (1F), 53.0 (2F), 54.8 (1F)ppm (External Standard: CF$_3$CO$_2$H).

(2) Synthesis of (+)-perfluoro-2-propoxypropionic acid chloride (+)-perfluoro-2-propionic acid 3.30 gr (10 mmol) was inserted into phosphorus pentachoride 2.50 gr (12 mmol) in ice bath. Upon completion of that addition, the substance was stirred for 10 minutes under the room temperature, and through careful distillation, acid chloride 3.24 gr (93%) was obtained. The boiling point; 73° to 74° C., $\alpha_D^{20}$+8.66° (neat, l=1).

(3) Synthesis of (+)-di(perfluoro-2-propoxypropionyl) methane

Isopropyl magnesium chloride (40 mmol) was synthesized in diethylether (20 ml). To the substance, acetate tertbutyl 4.64 gr (40 mmol) was added under the room temperature. The reaction was exothermic and propane gas was rapidly generated. The addition rate was adjusted so as to make the ether self-refluxed. Upon completion of the addition, after the substance was further stirred for a period of one hour, (+)-perfluoro-2-propoxypropionic acid chloride 6.54 gr (18 mmol) was added.

After the addition, the substance was stirred for a period of 15 minutes under the room temperature, thereafter it was quenched with dilute hydrochloric acid.

After separating an organic layer, the substance was dried with magnesium sulfate. After removing the ether and excessive reagent by means of fractional distillation, a small amount of p-toluenesulfonic acid was added, and the mixture was heated at 120° C. for a period of 15 minutes. The material-property values and spectrum analysis values were:

Yield: 5.20 gr (90%).
Boiling point: 94°~96° C./110 mmHg.
$[\alpha]_D^{28}$: +34.88° (neat, l=1).
IR (film): 1600 cm$^{-1}$ (C=O).
$^1$H NMR (CCl$_4$): 13.67, 5.97 ppm.
$^{19}$F NMR (CCl$_4$): δ 1.65 (1F), 4.00 (3F), 4.77 (3F), 6.55 (1F), 51.73 (2F), 57.50 (1F)ppm (External Standard: CF$_3$CO$_2$H).
Cu chelate: m.p.: 71°~72° C.

REFERENCE EXAMPLE 4

Europium chloride.6hydrate 0.73 gr (2 mmol) was dissolved into ethanol (7 ml). Into 50% water solution (6 ml) of 1 normal sodium hydroxide to which was added with 3.84 gr (6 mmol) of (+)-di(perfluoro-2-propoxypropionyl) methane, europium solution was added, and the mixture was stirred for a period of 2 hours under the room temperature. After that treatment, distilled water (10 ml) was added, and oil substance thus separated was extracted by means of pentane. After washing the pentane-extracted liquid with water, it was dried with magnesium sulfate.

When the solvent was removed through the vacuum distillation, and the substance was left as it was for a period of several hours under a temperature at 90° C. (0.8 mmHg), a yellow oily substance was obtained.

It was ascertained that it was an almost pure substance as desired (europium chelate) when it was examined with IR and NMR spectrum, the values below were measured:

Yield: 3.22 gr (78%).
IR (film): 1639 (C=O), 1530 (C=C)cm$^{-1}$.
$^1$H NMR(CF$_2$ClCFCl$_2$): δ 3.33 ppm.
$^{19}$F NMR (CF$_2$ClCFCl$_2$) δ 6.90 (6F), 7.57 (2F), 54.47 (2F), 61.83 (1F)ppm (External Standard: CF$_3$CO$_2$H).
$[\alpha]_D^{26}$: +48.52° (C 0.67, CF$_2$ClCFCl$_2$).

EXAMPLE 33

Synthesis of CF$_3$COCH$_2$COCF(CF$_3$)OCF$_2$CF$_2$CF$_3$

CF$_3$COCH$_2$Br (1.91 gr, 10 mmol), CF$_3$CF$_2$CF$_2$OCF (CF$_3$)CO$_2$C$_2$H$_5$ (3.58 gr, 10 mmol), and zinc powder (1.3 gr) were put into a flask (100 ml) together with a mixture comprising tetrahydrofuran (20 ml) and diethylformamide (10 ml), and subjected to the reaction for a period of one hour under the irradiation of ultrasonic waves generated by an ultrasonic cleaner (35W, 32 kHz).

After the reaction, impurities contained in the mixed liquid were filtered, and water (500 ml) was added to the filtered liquid, and an oily layer thus generated was extracted. After drying the extracted liquid with magnesium sulfate, the solvent was removed by means of fractional distillation. Through the distillation, the product (bp: 80° to 83° C./150 mmHg) was obtained with a yield by 58%. The spectrum analysis values of this product were:

Mass: M+ 440.

NMR: $^1$H (δ CDCl$_3$) 5.2(CH$_2$)ppm, $^{19}$F (δ) −11 (CF$_3$CO), 1.6 (1F), 4.2 (3F), 4.8 (3F), 6.6 (1F), 52 (2F), 58 (1F)ppm (External Standard: CF$_3$CO$_2$H).

What is claimed is:

1. A process for producing fluorine-containing organic compounds characterized in that fluorine-containing compounds which are at least one member selected from the group consisting of aliphatic iodides of R$_f$I, R$_f$ZnI, and R$_f$SnX$_2$I (where R$_f$ indicates a fluorine-containing aliphatic group; and X indicates halogen), and fluoroesters of R$_f$COOR' (where R$_f$ indicates a fluorine-containing aliphatic group; and R' indicates an aliphatic hydrocarbon group or aromatic hydrocarbon group) are reacted with organic compounds in the presence of ultrasonic wave action, whereby the R$_f$ group or the R$_f$CO group is introduced into the said organic compounds.

2. A process according to claim 1, wherein a carbonyl compound which is represented by the Formula: RCOR' (where R and R' represent similar or dissimilar atoms or groups which are selected from the group consisting of hydrogen atom, aliphatic group, and aromatic group, and where both of them are of the same aliphatic group, they are capable of forming rings jointly) is used as said organic compound, and is caused to react with said fluorine-containing aliphatic iodide in the presence of at least either zinc powder and halogenated tin powder which is represented by SnX$_2$ (where X represents halogen).

3. A process according to claim 1, wherein said fluorine-containing aliphatic iodide is caused to react with a halogen-substituted unsaturated compound having multiple bonds between carbon atoms, or a halogen-substituted aromatic compound in the presence of the action of ultrasonic waves and in the presence of zinc powder and palladium compound catalyst, whereby said R$_f$ is introduced into said multiple bond or aromatic nucleus, and whereby an unsaturated compound or an aromatic compound from which halogen is eliminated is obtained.

4. A process according to claim 3, wherein said halogen-substituted unsaturated compound is represented by the Formula:

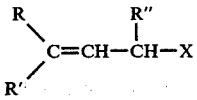

(where R, R' and R'' represent a hydrogen atom, an alkyl group or alkenyl group, having carbon atom numbers of 10 or less than 10, aromatic group or aromatic group substituted with a substituent and X represents halogen), or is represented by the Formula:

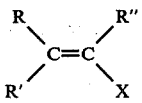

(where R, R' and R'' are the same as those described above, and X represents halogen); and as said halogen-substituted aromatic compound, a halogenated aryl compound or its derivative which is represented by the Formula:

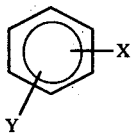

(where X represents halogen; and Y represents at least one type of a hydrogen atom or substituents which are selected from the group consisting of an alkyl group or alkenyl group having carbon atom numbers of 5 or less than 5, cyano group, nitro group, ester group and aryl group) is used.

5. A process according to claim 3 or claim 4, wherein the palladium compound catalyst is a divalent compound or Pd(O)Ln.

6. A process according to claim 3, wherein said halogen-substituted unsaturated compound is represented by the Formula:

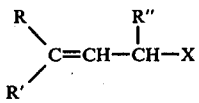

(where R, R' and R" represent a hydrogen atom, an alkyl group or alkenyl group, having varbon atom numbers of 10 or less than 10, or aromatic group or aromatic group which is substituted with a substituent; and X represents halogen, or is represented by the Formula:

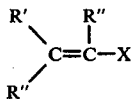

(wherein R, R' and R" are the same as those described before; and X represents halogen), and as said halogen-substituted aromatic compound, a halogenated aryl compound or its derivative which is represented by the Formula:

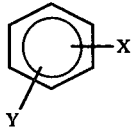

(where X represents halogens; and Y represents a hydrogen atom or at least one of substituents which is selected from the group consisting of an alkyl group or alkenyl group, having carbon atom numbers of 5 or less than 5, cyano gruop, nitro group, ester group and aryl group is used.

7. A process according to claim 6, wherein, the palladium compound catalyst is a divalent compound or Pd(O)Ln.

8. A process according to claim 1; wherein $R_f$ is a fluorine-containing alkyl group or alkenyl group having carbon atoms in the number of 10 or less.

9. A process according to claim 2 or claim 8, wherein R and R' are an alkyl group or alkenyl group having carbon atoms in the number of 15 or less.

10. A process according to claim 1 wherein zinc powder and/or halogenated tin powder are used within a range of one to three times $R_fI$, in the number of moles.

11. A process according to claim 1 wherein fluorine-containing aliphatic iodide and a carbonyl compound or a halogen-substituted aliphatic or aromatic compound are caused to react under the use of an aprotic polar solvent.

12. A process according to claim 1, wherein the reaction is caused under ambient temperature and atmospheric pressure.

13. A process according to claim 1, wherein fluorine-containing aliphatic iodide which is represented by the Formula:

$$R_fZnI \text{ or } R_fSnX_2I$$

(where $R_f$ represents fluorine-containing aliphatic group; and X represents halogen) is caused to react with a carbonyl compound which is represented by the formula:

$$RCOR'$$

(where R and R' represent similar or dissimilar atoms or groups which are selected from the group consisting of hydrogen atom, aliphatic group and aromatic group, and where both of them are of aliphatic groups, they are capable of forming rings jointly).

14. A process according to claim 13, wherein $R_f$ represents a fluorine-containing alkyl group or fluorine-containing alkenyl group having carbon atoms in the number of 10 or less.

15. A process according to claim 13 or claim 14, wherein R and R' are to be an alkyl group or alkenyl group having carbon atoms in the number of 15 or less.

16. A process according to claim 13, wherein the reaction is caused under ambient temperature and atmospheric pressure.

17. A process according to claim 13, wherein fluorine-containing aliphatic iodide which is represented by the Formula:

$$R_fI$$

(where $R_f$ represents a fluorine-containing aliphatic group) is caused to react with zinc powder and/or halogenated tin powder which is represented by SnX₂ (where X presents halogens) under heating, whereby $R_fZnI$ and/or $R_fSnX_2I$ is generated, and the product is used for the reaction.

18. A process according to claim 17, wherein zinc powder is used within a range of one to three times that of $R_fI$ in the number of moles.

19. A process according to claim 1,
(1) wherein halogenated ketone which is represented by the Formula;

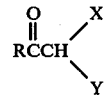

(where R represents an aliphatic hydrocarbon-oxy group, aliphatic hydrocarbon group or fluoro aliphatic hydrocarbon group, and includes those which are forming rings between carbon atoms being bonded with X; X represents halogen; and Y represents hydrogen atoms or fluorine atom) is caused to react with a metal (M) comprising zinc or magnesium, whereby a metallic halogenated ketone is generated which is represented by the Formula:

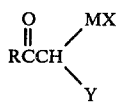

(where R, X and Y are the same as those described before; and M represents zinc or magnesium); and
(2) wherein the metallic halogenated ketone thus generated is caused to react with a fluoroester which is represented by the Formula:

(where $R_f$ represents a fluoroaliphatic hydrocarbon group, and includes those having ether bonds in their chains; R' represents an aliphatic hydrocarbon group or aromatic hydrocarbon group) in the presence of ultrasonic waves, whereby a fluorine-containing diketone is generated which is represented by the Formula:

(where R, Y and $R_f$ are the same as those described before.)

20. A process according to claim 19, wherein a halogenated ketone is caused to react with a fluoroalkylester under the action of ultrasonic waves in the presence of zinc or magnesium.

21. A process according to claim 19; wherein a halogenated ketone is caused to react with zinc or magnesium in the presence of ultrasonic waves to generate metallic halogenated ketone, and further this metallic halogenated ketone is caused to react with fluoroalkylester in the presence of ultrasonic waves.

22. A process according to claim 19, wherein metallic halogenated ketone is generated by making halogenated ketone and zinc or magnesium to react under heating, and further this metallic halogenated ketone is subjected to reaction with fluoroalkyl ester under the action of ultrasonic waves.

23. A process according to any one of claim 19 through claim 22, wherein, in at least one of aprotic polar solvents which is selected from the group consisting of tetrahydrofuran, dimethylformamide, acetonitrile, dimethlsulfoxide, dimethylacetamide, N-methylpyrrolidone and hexamethylphosphoamide, the reaction is caused to take place.

24. A process according to claim 19, wherein the number of carbon atoms of R is limited to 10 or less.

25. A process according to claim 24, wherein, as halogenated ketone, d-3-halogenated camphor is used.

26. A process according to claim 19, wherein X is to be of bromine atoms or iodine atoms.

27. A process according to claim 19, wherein $R_f$ is to be of a fluoroalkyl group or alkenyl group, or fluoroalkyl group or alkenyl group which is substituted and introduced with other halogens, all of which having carbon atoms in the number of 15 or less.

28. A process according to claim 19, wherein $R_f$ is to be of a fluoroalkylether group which is represented by the Formula:

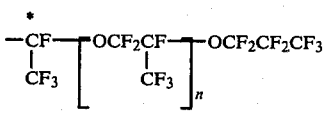

(where $n = 0 \sim 3$; and C* represents asymmetric carbon.)

29. A process according to claim 19, wherein R' is to be an alkyl group or alkenyl group having carbon atoms in the number of 10 or less.

* * * * *